United States Patent
Howett et al.

(10) Patent No.: US 6,458,346 B1
(45) Date of Patent: *Oct. 1, 2002

(54) BROAD SPECTRUM MICROBICIDAL AND SPERMICIDAL COMPOSITIONS, DEVICES, AND METHODS

(75) Inventors: Mary K. Howett, Hershey; John W. Krieder, Palmyra, both of PA (US)

(73) Assignee: The Pennsylvania State University, University Park, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/700,647

(22) PCT Filed: May 19, 1999

(86) PCT No.: PCT/US99/10956

§ 371 (c)(1),
(2), (4) Date: May 14, 2001

(87) PCT Pub. No.: WO99/59525

PCT Pub. Date: Nov. 25, 1999

Related U.S. Application Data

(63) Continuation-in-part of application No. 09/081,199, filed on May 19, 1998.

(51) Int. Cl.[7] .............................. A61F 6/04; A61F 6/10; A61K 31/74
(52) U.S. Cl. .................... 424/78.07; 424/422; 424/430; 128/837; 128/844; 128/918; 514/934
(58) Field of Search ................................ 424/424, 430, 424/422, 405; 128/844, 918, 837

(56) References Cited

U.S. PATENT DOCUMENTS

| 5,004,757 A | 4/1991 | Boucher |
| 5,143,720 A | 9/1992 | Lopes |
| 5,208,257 A | 5/1993 | Kabara |
| 5,380,754 A | 1/1995 | Miller et al. |
| 5,592,949 A | 1/1997 | Moench et al. |
| 5,617,877 A | 4/1997 | Moench et al. |
| 5,671,754 A | 9/1997 | Schmukler et al. |
| 6,177,441 B1 * | 1/2001 | Cook et al. .................. 514/297 |
| 6,033,679 A1 * | 4/2001 | Woo et al. .................... 424/401 |

FOREIGN PATENT DOCUMENTS

| EP | 0 465 423 A2 | 1/1992 |
| JP | 63287490 | 11/1988 |
| WO | WO-96 09761 A | 4/1996 |

OTHER PUBLICATIONS

Abstract of patent No. ZN 6707826 dated Apr. 1968.*
Enig, Mary G.—"Lauric oils as antimicrobial agents: theory of effect, scientific rationale, and dietary application as adjunct nutritional support for HIV–infected individuals" Chemical Abstracts, vol. 129, No. 7, Aug. 17, 1998, Columbus, OH, abstract No. 81130, XP002186940.
Supplementary European Search Report dated Jan. 25, 2002.
Database Caplus, AN 120:173556, Schmukler, et al., "Prevention of viruses from passing through the protective barrier materials." United States Dept. of Health and Human Services, USA, 1995, abstract.
Database Caplus on STN, AN:42966, Sucker, et al., "Pharmaceutical Formulations." Abstract.

(List continued on next page.)

Primary Examiner—Jose' G. Dees
Assistant Examiner—M. Haghighatian
(74) Attorney, Agent, or Firm—Dickstein Shapiro Morin & Oshinsky LLP

(57) ABSTRACT

Microbicidal and spermicidal devices, methods, and compositions containing sodium dodecyl sulfate or related anionic surfactants as active ingredients for the prevention and control of pregnancy and sexually transmitted disease, including conditions caused by non-enveloped viruses such as human papilloma virus.

6 Claims, 14 Drawing Sheets

OTHER PUBLICATIONS

World Patents Index, AN:90–066955, Saijo, et al., 1990, "Appts. For cleaning toner from copier–feeds to collector non–volatile material with affinity for toner particles." Abstract.

Database on STN: AN:26118, Skinner, et al., "Surface disinfectant active against microorganisms, both intro–and extracellularly." 1988. Abstract.

World Patents Index, Carella, et al., Composition for treating urogenital and intestinal disorders, e.g., caused by Candida strains–comprises Ericaceae plant(s) and growth factor for facilitating growth of lactic acid bacteria. Procter and Gamble Co. 1997, abstract.

Database Caplus on STN: AN 753698, Stewart, et al., "Stabilization of interferons for topical application." Dallas Biotherapeutics, Inc. 1995, abstract.

Database Caplus on STN, AN: 88–287490, Masayoshi "Method for Testing Mutagen." Organic Chemistry Microorganism industry, 1988, abstract.

Database Caplus on STN, AN Heleski, et al., "Detergent for washing up dishes, especially milk bottles and dairy containers." 1978, abstract.

Database Caplus on STN, AN:482904 Turevskaya, "Detergents in the milk industry." 1969, abstract.

Database Caplus on STN, Mashita, et al., "Detergent compositions for nursing bottles and tablewares." 1993, abstract.

D. Vollenbroich, et al. "Mechanism of Inactivation of Enveloped Viruses by the Biosurfactant Surfactin From *Bacillus Subtilis*", Biologicals Sep. 1997, 25(3):289–97, abstract.

"Tissue Xenografts as a Model System for Study of the Pathogenesis of Papillomaviruses", by M. K. Howett, et al., 1997, Elsevier Science Inc.

"Molecular Pathology of Human Oncogenic Viruses", by H.C. Isom, et al., 1996, Cellular and Molecular Pathogenesis.

"Toxicological Properties of Surfactants", by Ch. Gloxhuber, 1974, Arch. Toxicol.

"Toxicity of Sodium Lauryl Sulphate, Sodium Lauryl Ethoxysulphate and Corresponding Surfactants Derived from Synthetic Alcohols", by A.I.T. Walker, et al., 1967, Fd. Cosmet. Toxicol.

"Potentiated Acid 1,5 Pentanedial Solution–A New Chemical sterilizing and Disinfecting Agent", by R.M.G. Boucher, 1974, Amer. J. Hosp. Pharm.

"Ultrasonic Synergistic Effects in Liquid–Phase Chemical Sterilization", by G. Sierra, et al., 1971, Applied Microbiology.

"Measurement of Cavitation Activity in Ultrasonic Cleaners", by R.M.G. Boucher, et at., Contamination Control.

"Synergistic Effects in Sonochemical Sterilization", by R.M.G. Boucher, et al., 1967, Applied Microbiology.

"Evaluation of the Genotoxic Potential of Glutaraldehyde", by M.B.G. St. Clair, et al., 1991, Environmental and Molecular Mutagenesis.

"Collaborative Study of Mutagenicity With *Salmonella Typhimurium* TA102", by R. Jung, et al., 1992, Mutation Research.

"The Evaluation of Genotoxic Activities of Disinfectants and Their Metabolites", by Y. Sakagami, et al., 1988, Mutation Research.

Stewart, "Chemical Abstracts", vol. 123, #152951, 1995.

Skinner, et al., "Chemical Abstracts", vol. 108, #82144, 1988.

Carella, et al., "World Patents Index", vol. 97, #434711, 1997.

Sucker, et al., "Chemical Abstracts", vol. 85, #99180, 1976.

Schmukler, et al., "Chemical Abstracts", vol. 120, #173556, 1995.

* cited by examiner

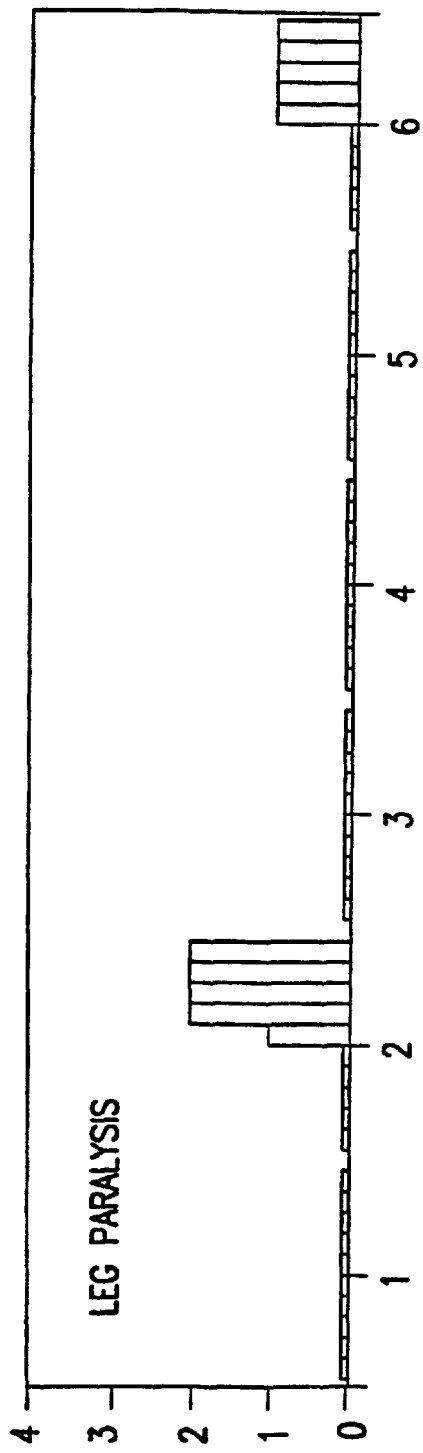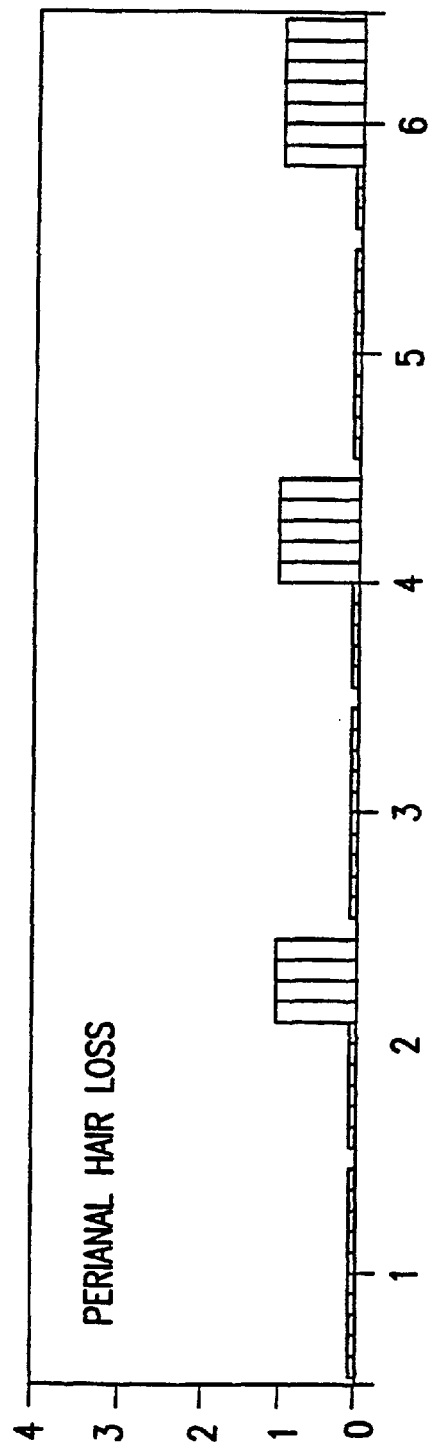

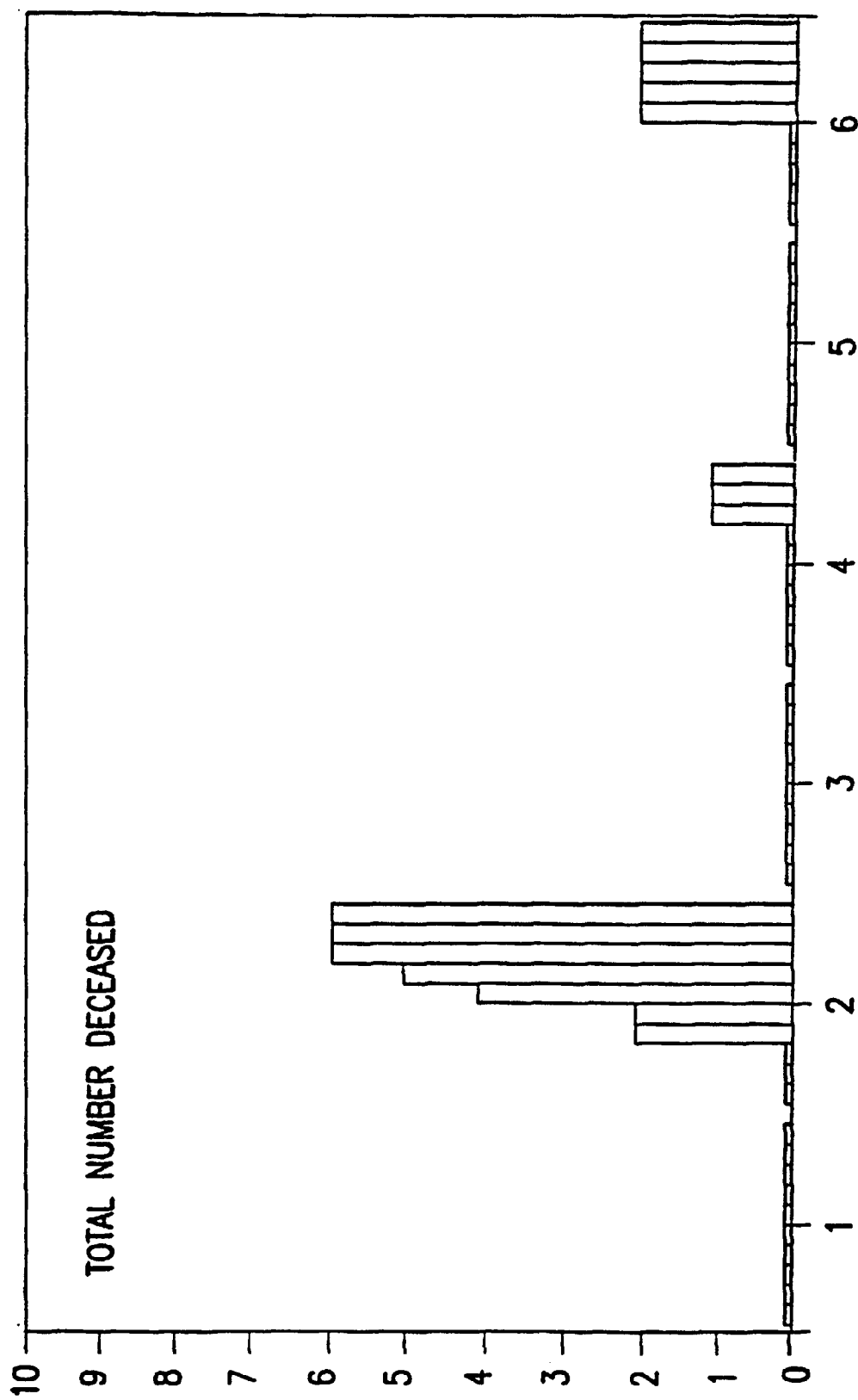

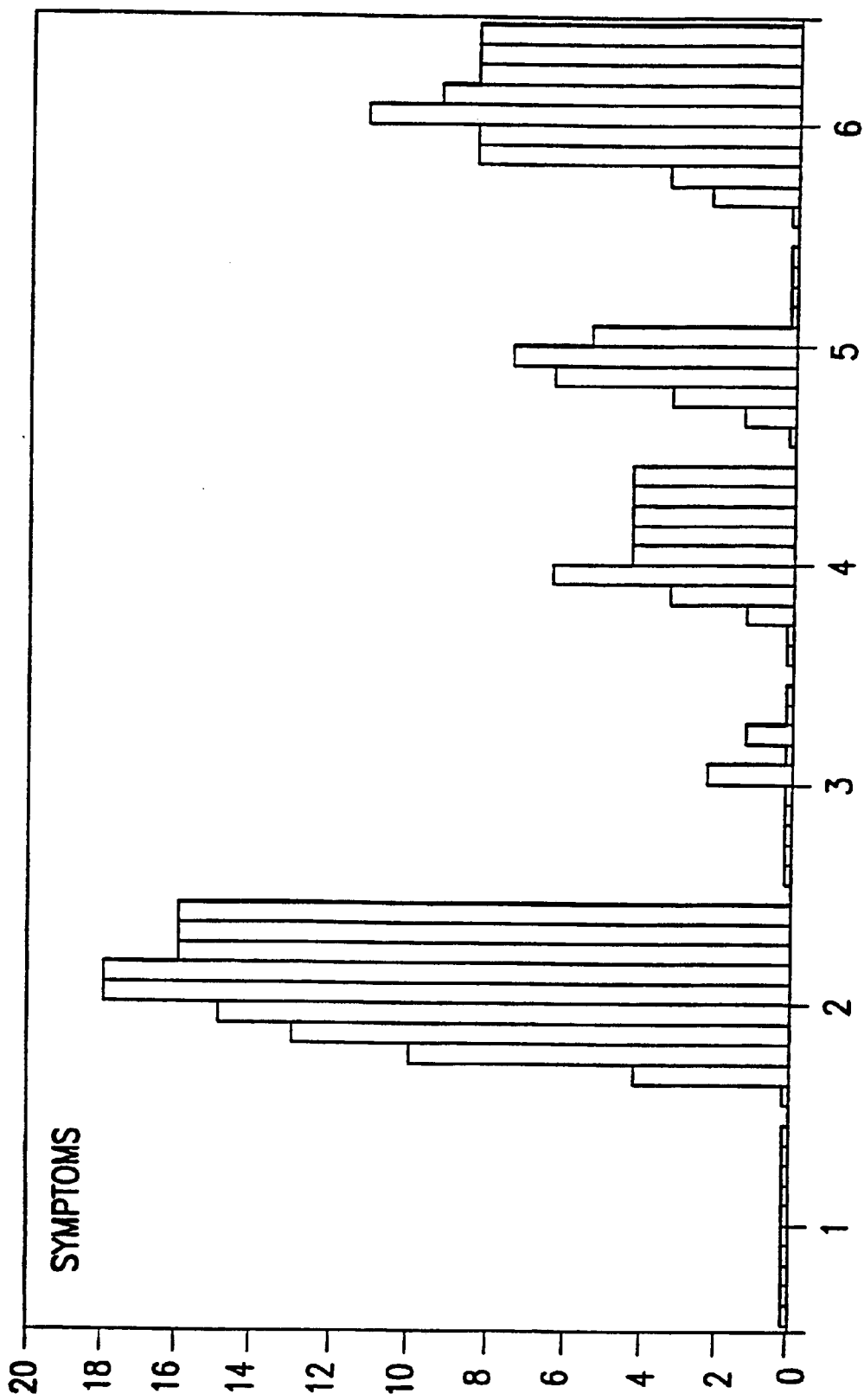

BROAD SPECTRUM MICROBICIDAL AND SPERMICIDAL COMPOSITIONS, DEVICES, AND METHODS

This application claims priority to International Patent Application No. PCT/US99/10956, filed on May 19, 1999, which is a continuation-in-part of U.S. patent application Ser. No. 09/081,199, filed on May 19, 1998.

U.S. GOVERNMENT RIGHTS

The United States Government has certain rights in the invention described and claimed herein as a result of its support of certain work related to the invention under a grant from the National Institute of Allergy and Infectious Diseases NIH Grant #5 P01 AI 37829-03.

FIELD OF THE INVENTION

The present invention relates to the prevention of pregnancy and the prevention and control of sexually transmitted and other diseases with the use of compositions having broad spectrum microbicidal and spermicidal activity, including the ability to inactivate particularly resistive pathogens such as human papillomaviruses and other non-enveloped viruses.

BACKGROUND OF THE INVENTION

Sexually transmitted diseases (STDs) are among the most prevalent and communicable diseases and continue to be a significant public health problem. It is e stimated that more than 250 million people worldwide, and close to 3 million people in the United States, are infected annually by gonorrhea. Annual worldwide incidence of syphilis is estimated at 50 million people, with 400,000 in the United States annually needing treatment. More recently, the human immunodeficiency virus (HIV), resulting in fatal acquired immunodeficiency syndrome (AIDS), has spread rapidly in both homosexual and heterosexual groups. The World Health Organization (WHO) and the National Institute for Health (NIH) recommend that mothers who are HIV positive not nurse their babies because of a high risk of transmitting HIV in breast milk. However, failure to nurse often results in infant malnutrition, diarrhea, dysentery, and other infectious diseases, because areas with high endogenous HIV often also have low food stores and poor hygienic quality of food and water.

Strong associations have now also been discovered between cervical cancer and papillomaviruses (PVs). It has been estimated that about 25% of women worldwide have human papillomavirus (HPV) genital infection. The human papillomaviruses (HPVs), of which there are now more than 90 known types, cause papillomas (warts) in a variety of human epithelial targets including common warts of the hands (verruca vulgaris) and feet (plantar warts), as well as genital warts in vulvar, vaginal, cervical and penile epithelium. Genital warts represent a ubiquitous STD. Women with genital lesions containing certain HPV types, including types 16, 18, 31, 33 and 35, are at increased risk for progression to cervical cancer. In the United States, 15,000 women per year are diagnosed with cervical cancer, and there are about 5000 deaths per year. In developing countries, cervical cancer is the leading cause of cancer related deaths among women.

PVs present a unique challenge for investigators attempting to identify virucidal agents. PVs are inherently extremely resistive to attack by antimicrobial agents. In addition, PVs do not exist free in nature in the same manner that many non-enveloped viruses exist. Rather, PVs exist encased in the squames of differentiated epithelial cells. Thus, the PVs are not only protected by their own very difficult to penetrate capsids, but also by the surrounding, heavily keratinized and cross-linked squames of epithelial cells.

One approach to the general control of STDs is the use of topically applied, female controlled microbicides that inactivate the relevant pathogens. Most frequently, these microbicides are spermicidal preparations containing NONOXYL-9 (N-9) detergent that inactivates enveloped viruses, such as HSV-2 and HIV-1. To date, these preparations have not been effective, however, against non-enveloped viruses such as the HPVs.

Inability to inactivate HPVs makes N-9 an inadequate virucide against this STD. In addition, chronic use of N-9 was recently associated with increased seroconversion for positivity to HIV-1 antibodies in a group of prostitutes, raising the possibility that N-9 may erode vaginal epithelium. Frequent use of N-9 is also positively correlated with bacterial vaginosis, genital ulcers and vulvitis, vaginal candidiasis, toxic shock syndrome, and epithelial disruption of the cervix and the vagina. The detergent, however, is spermicidal and has been shown to inactivate enveloped viruses. It is present in a large number of condoms and other spermicidal agents.

Other microbicides, such as octoxynol-9 (O-9), benzalkonium chloride (BZK) and chlorhexidine, are also surfactants that can disrupt the envelopes of HSV-2 and HIV-1 via surfactant/detergent properties. Like N-9, however, these microbicides also do not inactivate the non-enveloped PVs. Topical microbicides for inactivation of the PVs and prevention of animal or human transmission are currently not available, but would be highly desirable given the ubiquous nature of HPV infections.

U.S. Pat. No. 5,004,757 is directed to a method of deactivating viruses on surfaces by applying a three-part composition containing gluteraldehyde. The composition also contains hydrogen-bonded glycol molecules to eliminate aldehyde odor, and an anionic surfactant such as sodium dodecyl sulfate (SDS) as a potentiator of the virucidal activity of the gluteraldehyde component. The patent indicates that SDS has limited virucidal activity on its own, but has a synergistic effect when combined with gluteraldehyde. Due to the presence of gluteraldehyde, a well-known mutagen, the formulation is not useful against STDs or other diseases because it cannot be applied to human epithelium.

What is needed are safe and effective microbicides against STDs which extend microbicidal activity to non-enveloped viruses and, in particular, to papillomaviruses.

SUMMARY OF THE INVENTION

The present invention provides pharmaceutical compositions, articles and methods for preventing pregnancy and transmission of STDs, including safe and effective vaginal compositions for controlling and preventing STDs. The microbicidal compositions of the invention contain an alkyl sulfate, such as SDS, lithium dodecyl sulfate, lauric acids or salts thereof, as an active ingredient capable of inactivating sperm and a broad spectrum of pathogenic microbes, including HPVs and other non-enveloped viruses.

Additionally, the present invention provides articles and methods for inactivating infectious agents such as free HIV and cell-associated HIV as well as non-enveloped viruses, such as HPVs, human papoviruses, human picornavirus (hepatitis A virus), and human parvovirus, B-19, in biological fluids, including, for example, human and animal breast milk, serum and plasma. These articles and methods are provided by attaching SDS or an SDS derivative to a surface or gel matrix in contact with the fluid to be treated or by rapid surfactant removal of the SDS or SDS derivative from the fluid after treatment with the surfactant. In a particularly preferred embodiment, the surface having the surfactant attached thereto is positioned within a baby nursing bottle.

The invention also provides alkyl sulfate topical pharmaceutical compositions and methods for prophylactic avoidance and treatment of various medical conditions which involve bacterial or viral infection of the mucous membranes or skin.

The present invention also provides disinfectant compositions for destroying pathogenic microbes on medical instruments, shower stalls, bathroom fixtures, exercise equipment and other inanimate surfaces, as well as spermicidal barriers coated or impregnated with an alkyl sulfate compound for combined spermicidal and microbicidal effects.

It is interesting and surprising to note that, although SDS has been known for several years to have limited activity against enveloped viruses, and has been used as a surfactant for soaps, cosmetics and various other topical applications, such as shampoos and toothpastes, there have been no reports of its use, or the use of other topical antimicrobics, to control PVs. If indeed any such use occurred, it was unintended and unappreciated; it was an unrecognized accident. None of the reported studies or uses of SDS were conducted with the intent of controlling papillomavirus infections. Their purpose was merely as a surfactant/detergent, or at best as a facilitator of the antimicrobial activity of gluteraldehyde. There is, in fact, no known prior use of SDS for topical application which can be considered to have consistently achieved virucidal activity, as described hereinbelow.

BRIEF DESCRIPTION OF THE DRAWINGS

FIG. 1 shows the effects of SDS inactivation of cottontail rabbit papillomavirus (CRPV).

FIG. 2 shows the effects of SDS and N-9 treatment on CRPV.

FIGS. 3A through 3G demonstrate total symptoms per group of six groups of mice on days 3–12, for (A) swelling, (B) vaginal exudate, (C) redness, (D) death, (E) leg paralysis, (F) perianal hair loss and (G) any symptom, in an in vivo experiment on the toxicity of SDS and protection from vaginal infection with HSV-2.

DETAILED DESCRIPTION OF THE PREFERRED EMBODIMENTS

Figure 1A:
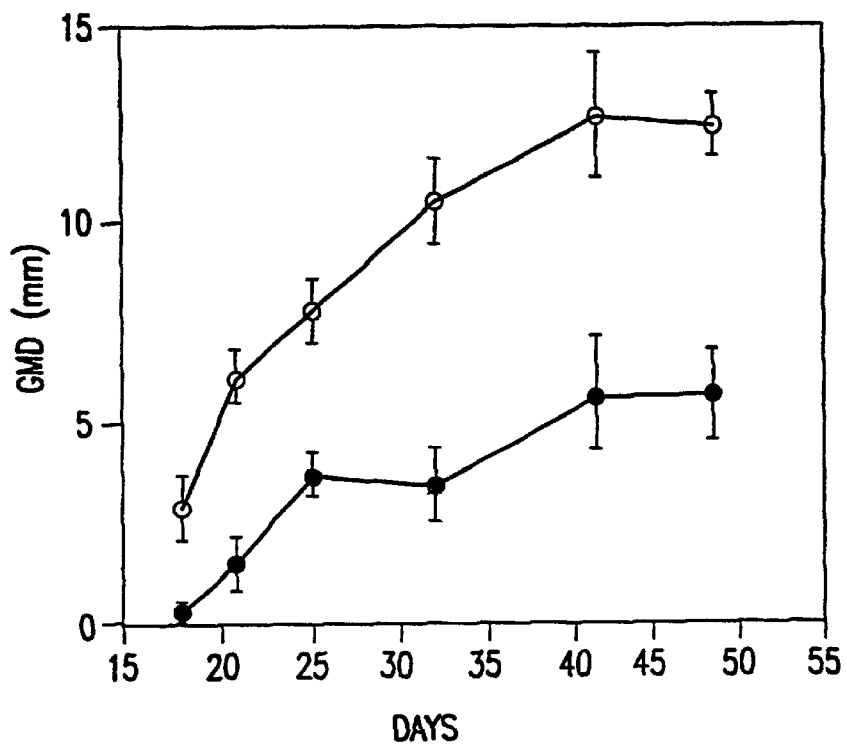
FIG. 1a demonstrates the average geometric mean diameter (GMD) of six lesions inoculated with normal (○) and with SDS-treated (•) CRPV.

We have discovered that SDS and related anionic surfactants have potent spermicidal and virucidal activity, including virucidal activity against non-enveloped viruses, including the papillomaviruses, as well as against HSV-2 and HIV-1. As used herein, "SDS or related anionic surfactant" means sodium dodecyl sulfate and other members of the virucidal alkyl sulfate group, including but not limited to lithium dodecyl sulfate, lauric acid and salts or other derivatives thereof.

In experiments conducted by the present inventors, very low concentrations of the detergent/sulfactant SDS completely inactivated HSV-2 and HIV-1, as well as three separate papillomavirus types after brief exposures to SDS at physiologic temperatures. In all cases, 0.1% concentrations of SDS were well above those exhibiting complete virus inactivation. Related anionic surfactants and derivatives also exhibited significant virucidal activity.

As used herein, "virucidal" means capable of inactivating or destroying a virus. A susceptible virus is any virus which is inactivated or destroyed by SDS or related anionic surfactants. The susceptible viruses are readily identified in tests such as those described below, wherein the amount or concentration of SDS or related anionic surfactant is considered virucidal if the virus titer is reduced by at least 99.9% (3 log units).

The invention can be carried out both in vitro and in vivo. In vitro means in or on nonliving things, especially on objects having hard or soft surfaces located or used where preventing viral transmission is desired. Hard surfaces include those of baby bottles, medical instruments, bags, catheters, tubing and other indwelling medical apparatus. Such surfaces also include building interiors, furniture, bathroom fixtures, gym equipment and exterior fences for, e.g., livestock containment. Soft surfaces include those of paper or cloth, for example, pre-moistened pads or tissues, dry facial tissues, hospital garments and bed clothing. In vivo means in or on a living person, plant or animal, especially on mammal skin and mucous membranes, including intravaginally, orally or rectally.

SDS or a related anionic surfactant can be used alone or in the form of a composition containing or consisting essentially of a virucidally effective concentration of SDS or related anionic surfactant and a pharmaceutically acceptable carrier. A virucidal effect can be achieved whether the composition is brought into contact with the virus or vice versa, whenever contact occurs with a known or potential locus of the virus. Virucidally effective concentrations of SDS or related anionic surfactant are generally in the range of about 0.05 to about 5.0 wt. percent, although a greater or lesser concentration may be used depending upon the particular circumstances.

The compositions of the invention include topical virucidal uses for both in vitro and in vivo purposes, especially for intravaginal use. For these purposes the SDS or related anionic surfactant can be formulated in any appropriate vehicle, provided that the surfactant and the vehicle are compatible, that is, that the microbicidal activity of the surfactant is not diminished by the vehicle. Thus, the compositions can be in the form of creams, foams, lotions, ointments, solutions or sprays. The carrier or vehicle diluent can be aqueous or non-aqueous, for example alcoholic or oleaginous, or a mixture thereof, and may additionally contain other surfactants, emollients, lubricants, stabilizers, dyes, perfumes, antimicrobial agents either as active ingredients or as preservatives, and acids or bases for adjustment of pH. The preferred pH is about 4 to 5. Conventional methods are used in preparing the compositions.

The preferred microbicidal and spermicidal agent for the compositions, articles and methods of the present invention is SDS. Preferably, the pharmaceutically acceptable carrier or vehicle for topically applied compositions is in the form of a liquid, jelly, or foam containing the surfactant. The surfactant can be incorporated into: (a) ointments and jellies, (b) inserts (suppositories, sponges, and the like), (c) foams, and (d) douches.

The topical composition may be prophylactically or therapeutically applied to human or other animal skin or mucous membranes for the prevention and treatment of various medical conditions caused by bacteria, enveloped viruses, and non-enveloped viruses. These conditions include, by way of example, lesions caused by herpes virus, apthous ulcers, acne, plantar and skin warts, respiratory papillomas, herpangina, herpetic esophagitis, molluscum contagiosum, hairy leukoplakia, and oral or genital Candida infections.

The topical composition is preferably introduced into the vagina of a female, at about the time of, and preferably prior to, sexual intercourse, but may also be administered to other mucous membranes. The compositions can be employed for the treatment and for protection against sexually transmitted diseases. The manner of administration will preferably be designed to obtain direct contact of the surfactant compositions of the invention with sexually transmitted microbes.

For topical applications, the pharmaceutically acceptable carrier may additionally comprise organic solvents, emulsifiers, geling agents, moisturizers, stabilizers, other surfactants, wetting agents, preservatives, time release agents, and minor amounts of humectants, sequestering agents, dyes, perfumes, and other components commonly employed in pharmaceutical compositions for topical administration.

Solid dosage forms for topical administration include suppositories, powders, and granules. In solid dosage forms, the compositions may be admixed with at least one inert diluent such as sucrose, lactose, or starch, and may additionally comprise lubricating agents, buffering agents and other components well known to those skilled in the art.

The compositions of the invention may also be impregnated into absorptive substrate materials, such as sponges, or coated onto the surface of solid substrate materials, such as condoms, diaphragms or medical gloves, to deliver the compositions to vaginal or other potentially infectable epithelium, preferably before or during sexual intercourse. Other articles and delivery systems of this type will be readily apparent to those skilled in the art. Among the presently preferred articles are condoms, which may be coated by spraying SDS onto the surfaces of the condoms, or by impregnating the SDS into the condom during manufacture by processes known in the art. Preferred coating compositions include silicon which provides lubricity and releases the surfactant in a time release manner. Bioadhesive polymers may also be used to prolong the time release aspects of the particular topical or other medicament employed.

The methods and compositions of the invention can be used to prevent and treat a broad spectrum of infections by pathogenic microbes. As used herein, "pathogenic microbes" is intended to include pathogenic bacteria, fungi, viruses, yeast, Chlamydia, or protozoans which do not normally reside in the host or which are capable of causing host pathology, and which are capable of being killed by SDS or related anionic surfactants, as described in detail herein.

Among the preferred pathogenic microbes for target by the compositions and methods of the invention are papillomaviruses (PVs), which represent a group of non-enveloped, icosahedral DNA viruses. The PVs induce benign neoplasms that can progress to cancers. Animal papillomas occur in a large number of species; certain viruses, such as the bovine papillomaviruses (BPVs) and the cottontail rabbit papillomavirus (CRPV), represent well-studied model systems. HPVs cause warts in epithelial target tissues. *Verrucae vulgaris*, plantar warts and genital condylomata all represent common clinical infections in humans. The compositions and methods of the invention have utility in preventing or controlling these human infections, and also preventing and controlling genital lesions containing HPV which can progress to malignancy, if left untreated.

Because cervical cancer is the number one cause of cancer related mortality in women in developing countries, effective prevention of HPV transmission should have significant impact on world health. Accordingly, a preferred method of the invention comprises contacting the virucidal compositions of the invention with HPVs transmitted to the vagina or other mucous membranes during sexual activity. The preferred mode of contact is by use of a condom coated or impregnated with, or by the use of a topical pharmaceutical composition containing, SDS in sufficient quantity to control or prevent HPV transmission and infection. The spermicidal activity of the active ingredients of the condoms and other articles and compositions of the invention provides an added benefit where the prevention of pregnancy is desired.

In addition, the SDS and related anionic surfactant compositions and methods of the invention may be broadly utilized as a disinfectant for effective inactivation of non-enveloped and enveloped, animal and human viruses on surfaces such as floors, medical instruments, bathroom surfaces, and gym equipment. The disinfectant composition containing SDS or related anionic surfactant is preferably incorporated into a spray-type dispenser whereby it can be sprayed directly onto the surface to be treated. An example of such use would be for a person to spray the composition on surfaces in public restrooms or gym equipment in order to kill any pathogenic microbes present from other persons who have used the facilities. The disinfection composition preferably contains SDS in solution or suspension with a diluent such as phosphate buffered saline at about 0.05 to 1.0 wt. % SDS.

A particularly preferred embodiment of the invention relates to inclusion of SDS or related anionic surfactants affixed to a solid surface (either the surface of plastic, or a similar material, or the surface of beads that can be in the form of, e.g., the matrix of a gel or filtration device). This embodiment includes, for example, containers or tubes for biological fluids, the surface of baby bottles, plastic nursing sleeves for baby bottles, or filters that may be incorporated into the nipple assembly of baby bottles or other containers or tubes for biological fluids. The surfactant is preferably covalently attached so that it is unable to leach out. This embodiment may be used to inactivate HIV and HIV containing cells in the breast milk of nursing mothers who are HIV positive.

Figure 4A:
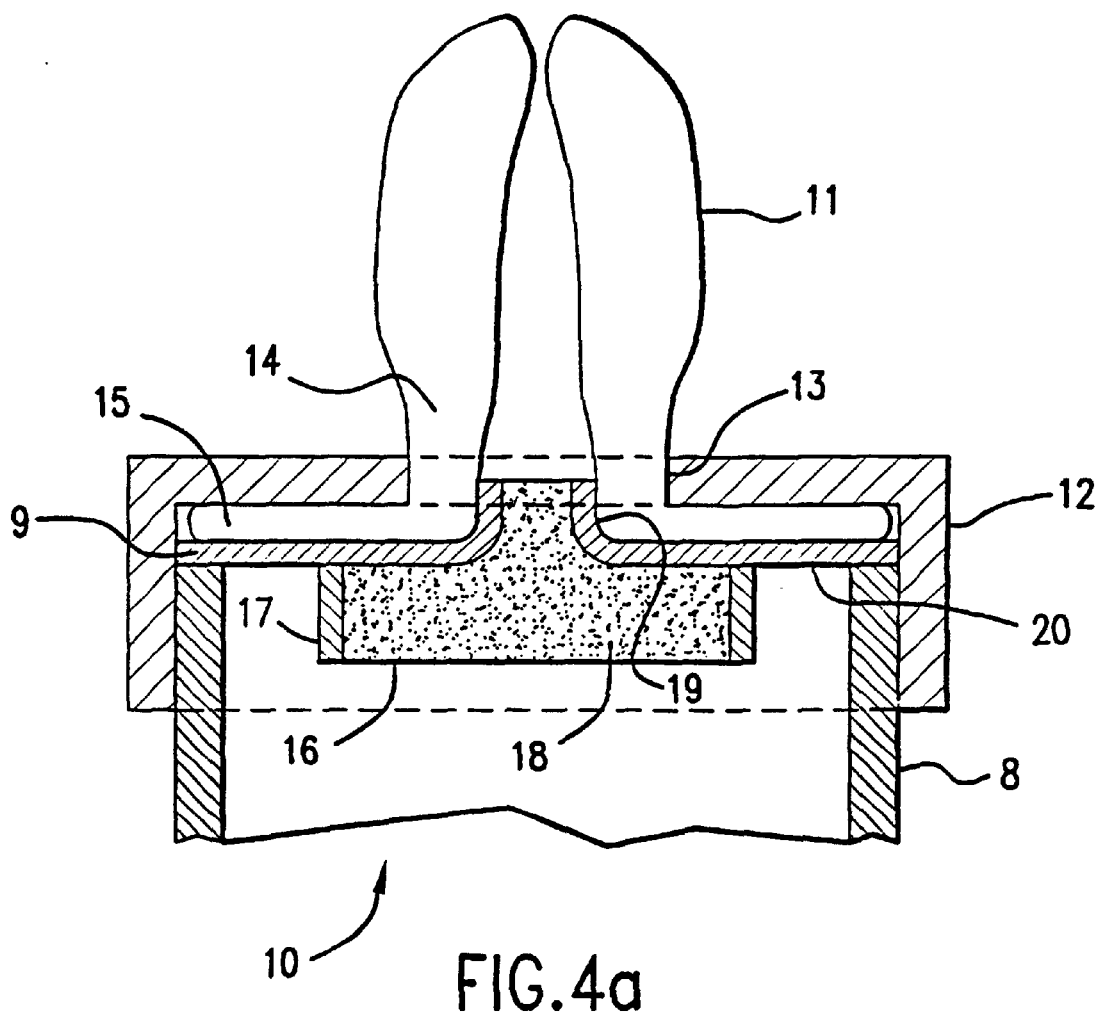
In FIG. 4(a) is shown a baby bottle nipple having a filter apparatus according to the invention.
Figure 4B:
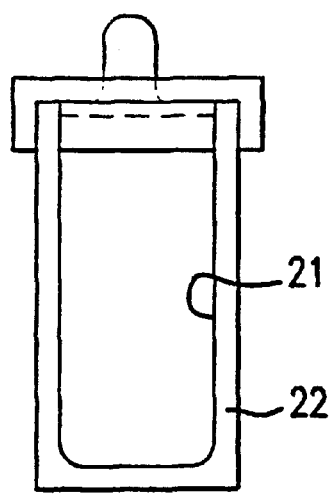
FIGS. 4(b) and (c) show baby bottles according to other embodiments wherein the alkyl sulfate microbicide of the invention is bound to the plastic bottle interior and to a nursing sack within the bottle, respectively.
Figure 4C:
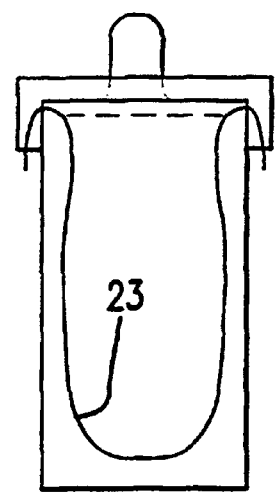

FIG. 4(*a*) shows a nursing bottle nipple apparatus 10, including a flexible nipple member 11, typically made of silicon or latex, and a cap 12 having a central orifice 13 from which an extending portion of the nipple 11 protrudes. Nipple member 11 includes a flange 15, which extends radially outward from the flexible nipple member. Filter unit 16 within cap 12 includes a housing 17 which contains a matrix material 18 therewithin. Filter unit 16 also includes a seal 9 having a shoulder 19, which extends a short distance within the hollow cavity of flexible nipple member 11. Seal 9 forms an annular flange 20 which extends radially between nipple flange 15 and the walls 8 of the nursing bottle when cap 12 is in place. Cap 12 may be held in place on bottle walls 8 via screw threads or the like.

Matrix material 18 may contain SDS or a related anionic surfactant attached to the matrix material, for example, a gel, beads or other filter material through which the breast milk may pass on its way from the interior of the nursing bottle to the baby's mouth. Accordingly, any cell-free HIV or cell-associated HIV virus from the mother's milk is inactivated by the surfactant before being ingested by the baby. Milk from a woman having HIV or other infection is thus pumped from the woman's breast and placed within the bottle. The nipple member and associated filter unit for HIV or cell-associated HIV inactivation of breast milk according to the present invention is then placed on the bottle with the bottle cap 12, flange 15 and seal 9 holding the filter unit 16 in place, so that the treated milk may then be fed to the baby while the milk is still warm.

Alternatively, matrix material 18 may include a material that will chemically remove SDS or related anionic surfactant. According to this embodiment, the surfactant may be mixed with the warm breast milk and then the milk may be fed to the baby through the nipple unit of the invention. In this manner, the HIV is inactivated by being mixed with the surfactant. The surfactant is then removed by the matrix during the feeding process.

As shown in FIGS. 4(b) and (c), the surfactant also may be attached to the inside surface 21 of a plastic baby bottle 22 or the inside of a plastic nursing sack 23. The milk may be pumped from the mother's breast and then placed within the bottle or sack containing the surfactant. The bottle and milk are preferably shaken for approximately minutes, and may be incubated and then fed to the baby. Preferably, the surfactant is covalently bound so that it resists leaching out into the milk. Any surfactant that might contaminate the milk can be removed by filter unit 16 containing a matrix material for rapid surfactant removal, so that the baby does not contract diarrhea from ingesting surfactant.

Similarly, the present invention is applicable to inactivation of viruses and other microbes in a wide variety of biological fluids besides breast milk. For example, various catheters, tubes and other indwelling apparatus may be combined with a filter unit having SDS or a related anionic surfactant or a surfactant removal material bound thereto or the surfactant may be attached to the interior surfaces of such apparatus. Accordingly, attachment of SDS or a related anionic surfactant to a solid surfaces may be used for microbicidal decontamination of biological fluids within containers, catheters, medical and pharmaceutical tubing and also within indwelling devices in patients. Attachment of SDS or related anionic surfactants to solid surfaces as taught herein also encompasses the surfaces of items used in food preparation such as cutting boards, and water and food containers.

Sodium dodecyl sulfate, $CH_3(CH_2)_{10}CH_2OSO_3Na$, and lauric acid, $CH_3(CH_2)_{10}COOH$, as well as the related anionic surfactants, all have microbicidal activity. The structure of SDS is provided by way of example below.

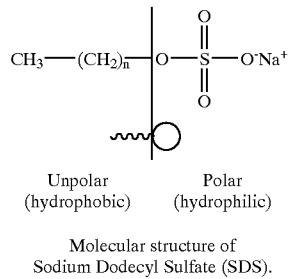

Unpolar (hydrophobic)    Polar (hydrophilic)

Molecular structure of Sodium Dodecyl Sulfate (SDS).

The surfactant molecules may be covalently bound to a filter unit or other substrate by any suitable method that does not interfere with the biological activity of the surfactant. In a preferred embodiment of the invention, the surfactant molecule is attached to silica (long chains of $SiO_2$) via an oxygen bond between $SiO_2$ and the acid end of the surfactant, via the hydoxyl or hydroxyl equivalent of the surfactant (e.g., the sodium sulfate end of SDS). For example, the OH on lauric acid is removed and the oxygen on the $SiO_2$ is removed. An oxygen bond then links the silicate to the CO end of the lauric acid. This method is used in the chemical industry to attach carbon chains of various lengths to silica matrix, the resulting substances being used as column materials for high pressure liquid chromatography. Glass is also composed of molten silicates and free silica groups are available at the surface. This approach may also be used to attach alkyl chain surfactants to the surface of glass baby bottles. This embodiment provides a method for attachment to any suitable surface including, for example, attachment to a beaded matrix.

In a second preferred embodiment, SDS or a related alkyl sulfate detergent is incorporated in or onto the surface of a plastic material. Suitable plastics include, for example, polyvinylchloride, polyethylene, polyurethane or silicone and other common substances for medical tubing, containers, and catheters, etc. These same substances can also be used to manufacture baby bottles or nursing sacks, or bags for serum and plasma. Surfactant bonding to plastic may also be accomplished via the hydroxyl, or hydroxyl equivalent position, of the surfactant molecule (leaving the fatty acid chain intact). The nature of the oxygen bonding can be adapted to various plastic substances and others by one of ordinary skill in the art given the teachings herein.

SDS or a related anionic surfactant may also be incorporated during the polymerization of the plastic polymer and then continuously leach out of the surface over a substantial period of time. Depending on the application for the plastic, for example baby bottles, it may be desirable to remove the surfactant after it has been allowed to leach into solution (breast milk). This approach would preferably use the impregnated plastic in combination with a surfactant removal matrix.

Thus, in addition to the covalent attachment of SDS and derivatives to solid surfaces, the present invention also provides devices and methods that encompass rapid removal of SDS and derivatives. This includes passage of surfactant treated biological fluids over any suitable chemical matrix for removing the surfactant. Several commercially available matrixes available for the removal of such detergents include, for example, Extracti-Gel R D Detergent Removal Gel and SDS-OUT SDS Precipitation Reagent, both available from Pierce Chemical Company, 3747 N. Meridian Road, P.O. Box 117, Rockford, Ill. 61105 and Detergent Adorber Gel polymer beads available from Roche Molecular Biochemicals, 9115 Hague Road, P.O. Box 50414, Indianapolis, Ind. 46250-0414.

With regard to the apparatus and methods of the present invention for the inactivation of infectious agents including non-enveloped viruses in serum and plasma, the conventional method for doing this involves Triton X-100, but this is recognized not to inactivate non-enveloped viruses. Very large batches of serum and plasma are produced in efforts to make clotting factor, antibody preparations, etc. Following surfactant treatment, the Triton is removed by filtration over columns which remove the detergent. There is increasing evidence that a number of non-enveloped viruses are present in the serum. These could include human papovaviruses, human picornavirus and human parvovirus. Human papovaviruses, such as the JC virus, is circulating in the human population, latent in most people, but can cause a uniformly fatal central nervous system disease called progressive multifocal leukoencephalopathy in 5–8% of AIDS patients. This virus is in the same family as the HPVs and is also inactivated by SDS and derivatives. The human picornavirus, hepatitis A virus, enters the body via the oral route, replicates in the intestine and spreads to the liver via the blood. This virus causes an acute hepatitis with 1% morality. The human parvovirus, B-19, causes fifth disease but can be fatal in a small number of pre-disposed individuals. This virus enters the body by the respiratory route, replicates in the oropharynx and is then found in large amounts in the blood. The removal of these infectious agents from the blood pool is a public health issue of most importance.

Dosage levels and concentrations of the surfactant in the compositions, articles and methods of the invention may be varied so as to obtain amounts in contact with the sexually transmitted or other biological fluids to obtain the desired therapeutic or prophylactic response for a particular surfactant and method of administration. Accordingly, the selected dosage level or concentration will depend on the nature and site of infection, the desired therapeutic response, the route of administration or contact, the desired duration of treatment or contact and other factors. Generally, the preferred concentration and dosage for SDS will be in the range of about 0.05 to 2.0 wt. percent. A preferred topical vaginal dosage form is a cream or suppository as described above containing from 0.05 to 2.0 wt. percent of the composition according to the invention. In each treatment, typically twice daily, from about 1 to about 5 ml of such dosage form is applied intravaginally, preferably high in the vaginal orifice. Greater amounts are generally avoided to minimize leakage.

SDS is of low intrinsic toxicity both to skin and mucous membranes. Preparations, such as shampoos and detergents that contact both skin and mucous membranes, contain dodecyl sulfate derivatives (sodium or ammonium dodecyl sulfate) in concentrations exceeding 10%. In addition, products that are routinely used in the oral cavity, such as toothpaste, have high (5–8%) concentrations of these compounds and are not acutely toxic to the oral mucosa. In the Examples provided below, virucidally effective concentrations of SDS were non-toxic in rabbit skin and in human newborn foreskin.

The examples described and discussed herein are intended to be illustrative of the present invention but not limiting. Numerous variations and modifications may be effected without departing from the scope of the novel concepts of the present invention.

EXAMPLE 1

Antiviral Activity of SDS

Materials and Methods

Chemicals

SDS was purchased from Bio-Rad (Richmond, Calif.) and filtered sterile solutions were made in phosphate buffered saline (PBS). N-9 was obtained from Rhone-Poulenec Rorer Pharmaceuticals Inc. (Collegeville, Pa.). All additional detergents were purchased from Boehringer Manheim (Indianapolis, Ind.). The following reagent was obtained through the AIDS Research and Reference Reagent Program, Division of AIDS, NIAID, NIH: HeLa-CD4-LTR-β-gal from Dr. Michael Emerman.

HSV-2 Inactivation Assay. HSV-2 (strain 333) virus stocks were propagated by low multiplicity infection of African Green monkey kidney (CV-1) cells and subsequent preparation of cell-free supernatants from frozen and thawed preparations of lytically infected cultures. Virus titers were determined by assay in CV-1 cell monolayers. Virus stocks were maintained in CV-1 cell culture medium which was Dulbecco's medium supplemented with antibiotics and 10% fetal calf serum. The protein concentration of the virus stocks was also increased by serum proteins and by cellular proteins released by the freezing and thawing of the infected cells.

For inactivation of HSV-2, 39 μl of virus was mixed with 1 μl of a 40×concentrated solution of detergent and then incubated at 37° C. for 10 min. After inactivation, the 40 μl of virus sample was diluted to 4 ml (1:100) using cell culture medium, and 1 ml of the diluted virus was adsorbed onto CV-1 monolayers for 1 hr at 37° C. Following adsorption, monolayers were refed and incubated at 37° C., 5% $CO_2$. Between 20 and 24 hr post infection, monolayers were fixed, stained with crystal violet and plaques counted using a dissecting microscope. The numbers in Table 1 each represent an average of 2 plates.

HIV-1 Inactivation Assay. One day prior to the assay, HeLa-CD4-LTR-β-gal cells were seeded into 12-well culture dishes at a concentration of $8 \times 10^4$ cells per well. A high titer ($10^{7.17}$ $TCID_{50}$/ml) virus stock of HIV-1 (strain IIIB; Advanced Biotechnologies, Inc., Columbia, Md.) was diluted 1:10 with RPMI 1640 supplemented with 10% FBS. To assess viral inactivation by SDS, 78 μl of diluted virus were mixed with 2 μl of detergent solution, and incubated for 10 min at 37° C. After the inactivation period, the virus and detergent were diluted with 720 μl R10 (1:10) supplemented with DEAE dextran (20 μg/ml final concentration). Aliquots of treated virus (300 μl) were then added to duplicate wells of HeLa cells and incubated at 37° C. for 2 hr. Following viral adsorption, 2 ml of fresh media (DMEM supplemented with 10% FBS, 0.1 mg/ml G418, and 0.05 mg/ml hygromycin B) were added to each well. After incubation at 37° C. and 5% $CO_2$ for 48 hr post-infection, cells were fixed and stained for β-galactosidase expression.

BPV-1 Focus Assay. Cell-free stocks of BPV-1 were prepared by extraction (10% w/v) of epidermal bovine warts in phosphate buffered saline (PBS). In order to detect the transforming ability of BPV-1, C127 mouse cells were seeded ($3 \times 10^5$ cells per flask) into $T-25^2$ flasks. After 24 hr of growth, subconfluent cells were infected with BPV-1. For the positive controls, stock virus (20 μl) was diluted (1:1) with PBS, incubated at 37° C. for 10 min, diluted 1:10000 and then added (100 μl) into the 5 ml of cell culture medium present on the cells. Cells were refed at 24 hours and subsequently 2 times weekly. The presence of morphologically transformed foci was counted after 2 weeks and then again at 3 weeks.

Virus inactivations were carried out in vitro by addition of concentrated SDS solutions to the virus stocks (20 μl of virus plus 20 μl of detergent) and subsequent incubation at 37° C. for 10 or 30 min as indicated. Following inactivation, virus was diluted 1000 fold to lower the detergent concentration and the preparations were immediately used for infection as above.

Shope Papilloma Induction. Stocks of Shope CRPV were prepared from papillomas generated in wild cottontail rabbits. Virus stocks were cell free extracts (10% w/v) of papillomas in PBS. Shaved dorsal skin was lightly scarified with a razor blade. Virus stocks were used to inoculate domestic cottontail rabbits (Hazelton Research Products, Denver, Pa.); a 40 μl aliquot of virus was dropped onto the surface of 4 locations on the dorsal skin. The 2 left sites on each rabbit received untreated virus and the 2 right sites received treated virus. Inactivation of either a $10^{-1}$ or $10^{-2}$ solution of virus stock was accomplished by addition of concentrated SDS solutions which were 40×the final indicated concentrations. Incubation of SDS and virus was at 37° C. for 10 min and virus was immediately used for inoculation of rabbits. Virus was not subsequently diluted following inactivation and the concentration of SDS present during inactivation and inoculation was 0.05%. Papillomas were first observed to develop in control sites around 2 weeks after inoculation. The geometric mean diameter (GMD) of all visible lesions was measured and is equal to the cube root of the length×width×height of the lesions as measured in mm by calipers.

Human Papilloma Induction. Stocks of experimentally generated infectious HPV 11 were prepared and represented 10% w/v cell free extracts of virus in PBS. Undiluted aliquots of virus stocks (39 μl) were mixed with a 40×solution of SDS 1 μl), incubated at 37° C. for 10 min and immediately used to infect split thickness grafts of newborn human foreskin epithelium. Virus was not subsequently diluted. Control grafts were infected with untreated virus stock. Virus adsorption was for 1 hr at 37° C. The concentration of SDS present during the inactivation period and during virus adsorption was 0.05%. Grafts were then transplanted beneath the renal capsule of athymic mice. Animals were maintained in isolator bubbles with antibiotic supplemented drinking water in the animal colony of the Hershey Medical Center. Three months following infection, animals were sacrificed, their kidneys were removed, and the xenografts were grossly examined. The remaining organs were examined for any apparent abnormalities and none were found. Portions of each graft were immediately fixed in 10% neutral-buffered formalin and processed by standard histologic techniques for staining with hematoxylin and eosin.

A second set of control grafts was exposed only to identical concentrations of SDS and no virus. These grafts were harvested on days 1, 5, 11 and 20 following transplantation in order to follow the viability and growth of the grafts after SDS exposure.

Results

Inactivation of the Infectivity of HSV-2 by SDS. In five separate experiments, treatment concentrations of SDS as low as 0.0125% to 0.025% were effective in eliminating the ability of the virus to induce plaques in a monolayer of monkey kidney cells (Table 1). Total HSV-2 inactivation was achieved with SDS concentrations between 0.0025% and 0.0125%. These effective concentrations are similar to the concentrations of N-9 needed for destruction of HSV infectivity (data not shown).

TABLE 1

| *% SDS during treatment | **% final SDS | Plaques/Plate (5 experiments) |
|---|---|---|
| 0 | 0 | 57/73/343/145/145 |
| $1 \times 10^{-1}$ | $1 \times 10^{-3}$ | 0/0/0/0/0 |
| $5 \times 10^{-2}$ | $5 \times 10^{-4}$ | 0/0/0/0/0 |
| $2.5 \times 10^{-2}$ | $2.5 \times 10^{-4}$ | 0/0/0/0/0 |
| $1.25 \times 10^{-2}$ | $1.25 \times 10^{-4}$ | 0/0/0/0/0 |
| $2.5 \times 10^{-3}$ | $2.5 \times 10^{-5}$ | 28/54/322/145/104 |

*Sterile SDS sticks if 40× of the treatment concentration were added to virus aliquots to achieve the treatment concentration. After mixing, samples were incubated at 37° C. for 10 minutes.
**Following SDS treatment, virus stocks were diluted 100 fold and 1 ml aliquots were immediately adsorbed onto CV-1 cells. Plaques were counted after 20–24 hours of infection. Each number represents an average of 2 plates.

Inactivation of the infectivity of HIV-1 by SDS and the non-ionic detergent C31G. It is established that N-9 can inactivate HIV-1. We compared inactivation of HIV-1 by a second non-ionic detergent, C31G, and by SDS. High titer virus stocks of HIV-1 were incubated with either C31G or SDS and then virus was assayed on indicator cells expressing β-gal under the control of the HIV-1 LTR. After 48 hours, cells were stained and the number of cells expressing increased β-gal counted. Both of these detergents were highly effective in the inactivation of HIV-1 (Table 2). Total inactivation of HIV-1 was achieved with C31G concentrations as low as 0.0125% and with SDS concentrations as low as 0.025%.

TABLE 2

| % C31G during treatment | *% cells expressing LTR-β gal gene (duplicate wells) | cells counted |
|---|---|---|
| $5 \times 10^{-2}$ (toxic) | 0, 0 | >$10^6$ |
| $2.5 \times 10^{-2}$ | 0, 0 | >$10^6$ |
| $6.25 \times 10^{-3}$ | 19 +/− 6.1, 19 +/− 6.4 | 1080, 805 |
| $2.5 \times 10^{-3}$ | 22 +/− 7.4, 29 +/− 8.1 | 1620, 1820 |
| % SDS during treatment | | |
| $5 \times 10^{-2}$ | 0, 0 | >$10^6$ |
| $2.5 \times 10^{-2}$ | 0, 0 | >$10^6$ |
| $1.25 \times 10^{-2}$ | 24 +/− 3.3, 24 +/− 10 | 2810, 2190 |
| $6.25 \times 10^{-3}$ | 10 +/− 1.7, 15 +/− 2.1 | 2390, 2290 |
| $2.5 \times 10^{-3}$ | 9 +/− 5.5, 11 +/− 3.5 | 1940, 1910 |
| Mock Infected Cells | 0, 0 | >$10^6$ |
| HIV-1 Infected Cells | 17 +/− 4.8, 24 +/− 5.4 | 2680, 1480 |

*Five random fields of cells were counted in each plate displaying blue cells.
*Duplicate plates were assayed for each sample; individual numbers are the standard deviation within 5 fields of one plate.

Destruction of the Ability of BPV-1 to Induce Morphologically Transformed Foci in Monolayers of C127 Mouse Cells. Although SDS could effectively reduce HSV-2 infectivity, it remained possible that this destruction was mediated by envelope removal. Because papillomaviruses are non-enveloped, the possibility remained that SDS would fail to inactivate these viruses. We utilized BPV-1 as a prototype PV because of its ability to rapidly (within 2 weeks) form multi-layered transformed foci in mouse fibroblasts in an in vitro assay. Table 3 describes results of two separate experiments in which stocks of BPV-1 were incubated at 37° C. with various concentrations of SDS (5% to 5×$10^{-4}$%) for either 10 or 30 minutes, diluted to lower the SDS concentration (to avoid cell toxicity) and then used to infect C127 cells. Following incubation of control or infected cultures, foci were counted at 14 and 17 days after infection. Results indicate that SDS in concentrations as low as 0.05% or 0.005% can totally inactivate BPV-1 transforming ability after treatment of the virus at 37° C. for 10 or 30 minutes, respectively. Inactivation of BPV-1 by the lower concentration of 0.005% after 30 minutes indicated that inactivation is proportional to time as well as to detergent concentration. Table 4 lists several other commercially available detergents that were tested for possible inactivation of BPV-1. None of these detergents inactivated the morphologic transforming properties of the BPV-1.

TABLE 3

| *% SDS during treatment | **% final SDS | foci/plate Exp. 1 Day 12 | foci/plate Exp. 2 Day 14 | Day 17 |
|---|---|---|---|---|
| 0 | 0 | 266 | 255 | 153 |
| 5 | $5 \times 10^{-3}$ | 0 | N.D. | N.D. |
| $5 \times 10^{-1}$ | $5 \times 10^{-4}$ | 0 | N.D. | N.D. |
| $5 \times 10^{-2}$ | $5 \times 10^{-5}$ | 0 | 0 | 0 |
| $5 \times 10^{-3}$ | $5 \times 10^{-6}$ | 0 | 271 | 150 |
| $2.5 \times 10^{-3}$ | $2.5 \times 10^{-6}$ | N.D. | 273 | 162 |
| $5 \times 10^{-4}$ | $5 \times 10^{-7}$ | N.D. | 229 | 151 |

*Sterile SDS stocks of 40x the treatment concentration were added to virus aliquots to achieve the treatment concentration.
**Following virus treatment, treated virus stocks were further diluted 1:1000 in order to dilute the detergent
In Experiment 1, virus and SDS were mixed and incubated at 37° C. for 30 minutes.
In Experiment 2, virus and SDS were mixed and incubated at 37° C. for 10 minutes.
N.D. = not done In control plates, without BPV-1, no foci appeared.

TABLE 4

Detergents that failed to inactivate BPV-1 morphologic transformation of C127 cells Nonoxynol-9
C31G
3-[(3-cholamidopropyl)-dimethylammonio]-2-hydroxy-1-propane sulfonate (CHAPSO)
N-dodecyl-N, N-dimethyl-3-ammonio-1-propane sulfonate
3-[(3-cholamidopropyl)-dimethylammonio]-1-propane sulfonate (CHAPS)
isotridecylpoly (ethylene-glycolether)$_n$
octanoyl-N-methyl-glucamide (MEGA-8)
Triton X-100
Thesit All detergents except C31G and N-9 were purchased from Boehringer-Mannheim, N-9 was purchased from Rhone-Poulenec Rorer Pharmaceuticals, C31G was provided by Biosyn, Inc.
None of the above reduced foci.
Positive control SDS @ 1% completely eliminated virus foci.
All detergents were incubated with virus; 1% final concentration, 37° C., 10 min.

Figure 1B:
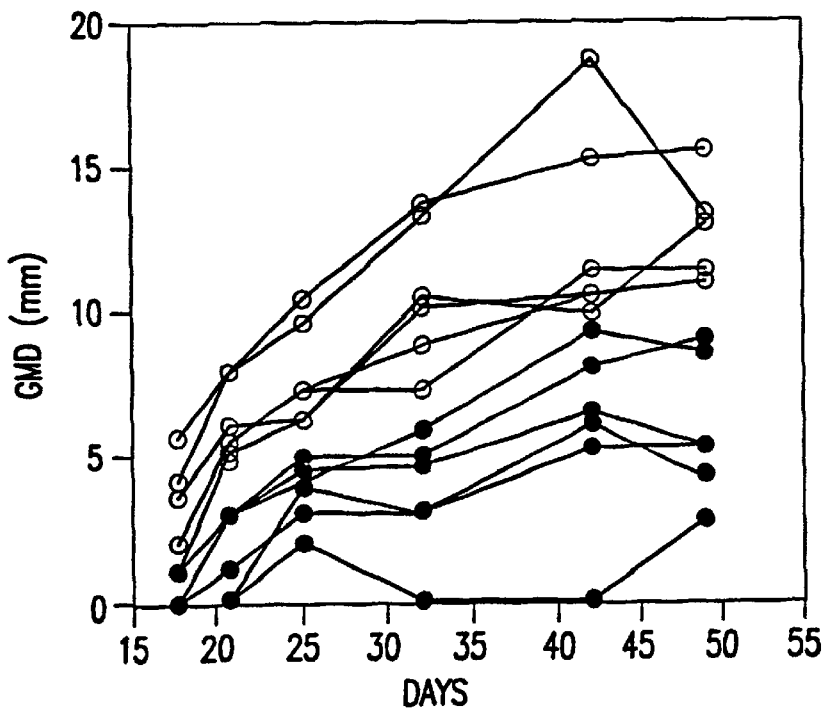
FIG. 1b demonstrates the growth of individual lesions.

Effect of SDS Inactivation of CRPV on Formation of Shope Papillomas in Rabbits. To extend the observation of PV inactivation by SDS to an in vivo animal model system, we utilized the well established CRPV model system. A standard CRPV stock known to form papillomas with 100% efficiency was used. The infectious dose 50 ($ID_{50}$) for the virus stock corresponds to 50 µl of a $10^{-3}$ dilution of the stock virus. In our experiments, 40 µl of a $10^{-1}$ dilution and subsequently 40 µl of a $10^{-2}$ dilution of the virus stock solution were used. Both of these concentrations far exceeded the $ID_{50}$. SDS was mixed with virus to a final concentration of 0.05% and subsequently incubated at 37° C. for 10 min. Immediately following incubation, virus was inoculated by skin scarification of the backs of the rabbits. Inoculated sites contained two untreated (left; L) and two treated (right; R) virus samples on the same rabbit. Figure 1a demonstrates the average GMD of six lesions inoculated with normal ($10^{-1}$ dilution) and six lesions inoculated with SDS-treated CRPV. GMDs were measured and compared on post inoculation days 18, 21, 25, 32, 42 and 50. Results indicate that a $10^{-1}$ dilution of virus stock was substantially inactivated by a 10 min, 0.05% SDS treatment at 37° C. FIG. 1b shows the growth curves over 50 days following inoculation for each individual lesion. It should be noted that each of the six sites that received SDS treated preparations (•) were delayed in the development of papillomas, indicating a substantial inactivation of virus. Once papillomas developed, however, the growth rate of the lesions appeared similar to the ones that developed from the untreated inoculum.

Figure 2A:
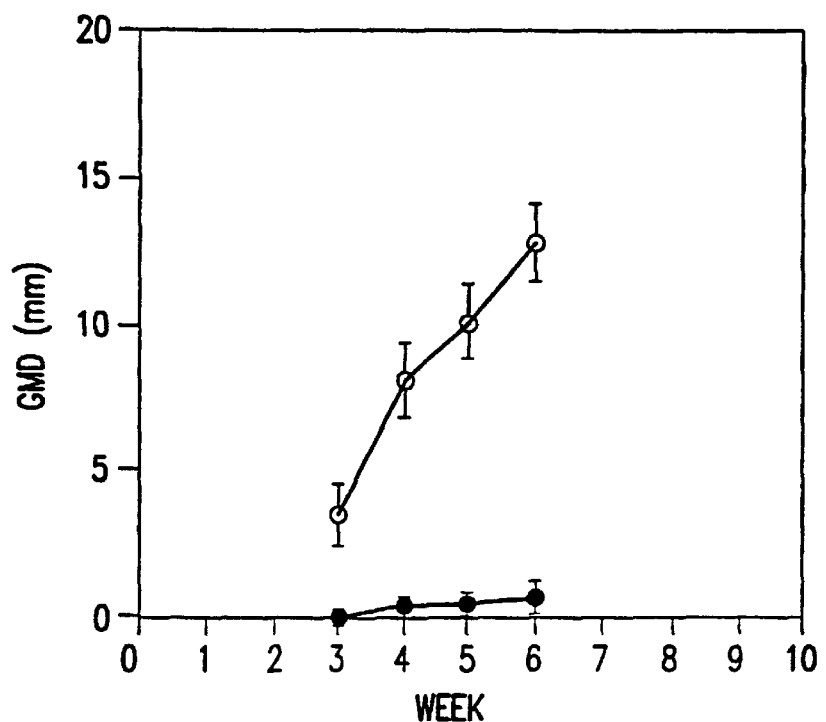
FIG. 2a demonstrates the GMD of ten inoculation sites that received SDS treated virus (•) compared to 10 sites that received normal virus (○).

In a subsequent experiment (FIGS. 2a and 2b), a $10^{-2}$ dilution of CRPV virus stock was also incubated at 37° C. for min with either 0.05% SDS or 0.05% N-9. This dilution of the stock virus not only contained less virus but also a lower total protein concentration. Following incubation, detergent treated and control virus samples were inoculated into five rabbits for the N-9 samples and five rabbits for the SDS treated samples. Untreated virus samples were also inoculated onto the same rabbits at different sites. This experiment was undertaken for two purposes: to observe the inactivation of a smaller amount of CRPV by SDS and to directly compare inactivation with SDS to that achieved by the N-9 treatment. As in the previous experiment, the left inoculation sites (two per animal) received untreated virus and the right inoculation sites (two per animal) received treated virus. FIG. 2a shows the GMD of ten inoculation sites that received SDS treated virus compared to ten inoculation sites that received normal virus. GMDs were measured 3, 4, 5, and 6 weeks after virus inoculation. In 8 of 10 sites inoculated with SDS treated virus, papillomas failed to develop; the remaining 2 sites developed very small papillomas beginning to appear 4 weeks after inoculation. Although quantitative measurements were not performed, the SDS inoculated sites did not exhibit any irritation during the experiment. In the 10 sites inoculated with normal CRPV, papillomas developed in 10 of sites within 2 weeks after inoculation and grew progressively.

Figure 2B:
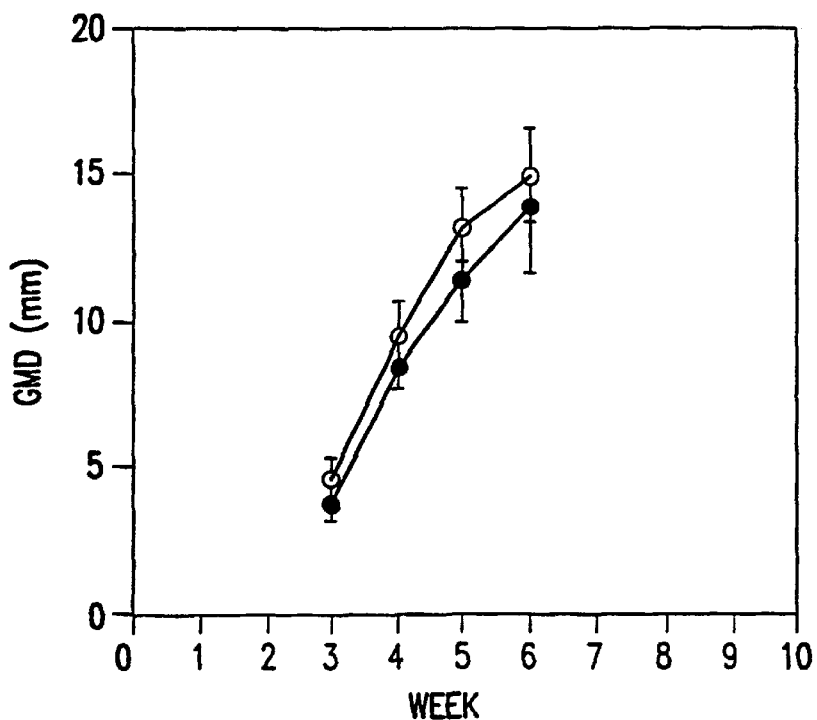
FIG. 2b shows comparative growth of papillomas in 10 sites that received normal CRPV (○) compared to 10 sites that received CRPV treated with N-9 (•).
Figure 3C:
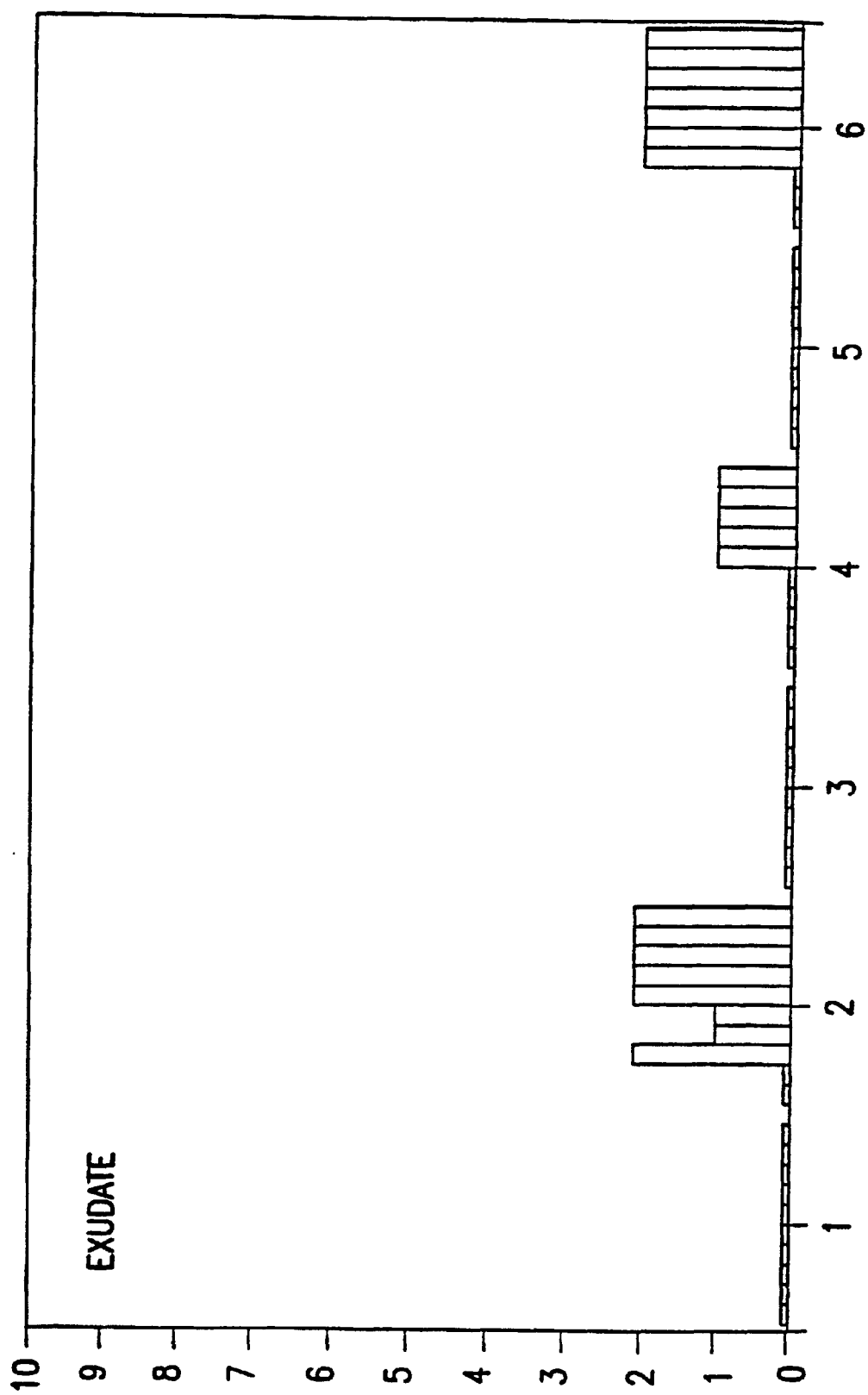
Figure 3D:
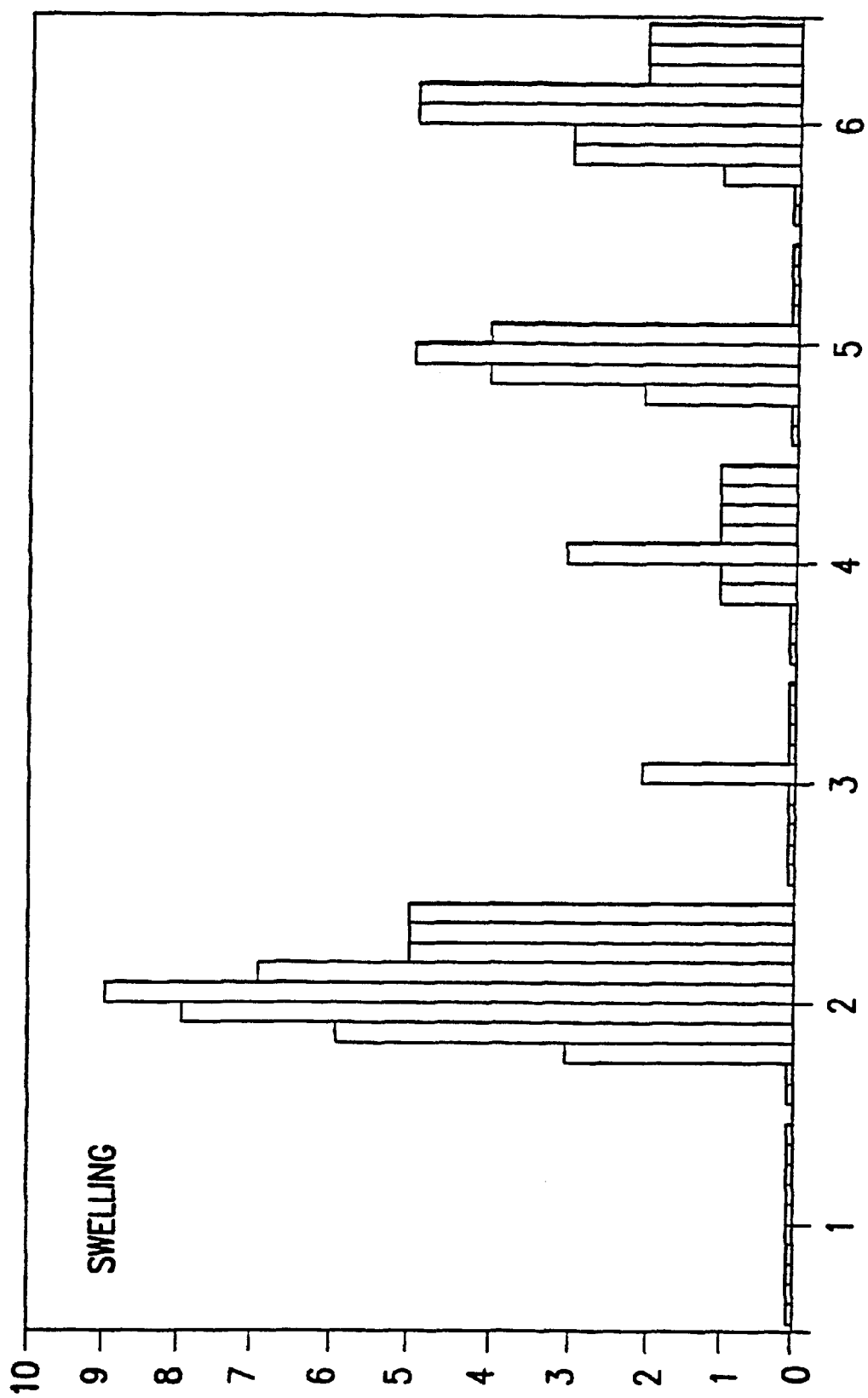
Figure 3E:
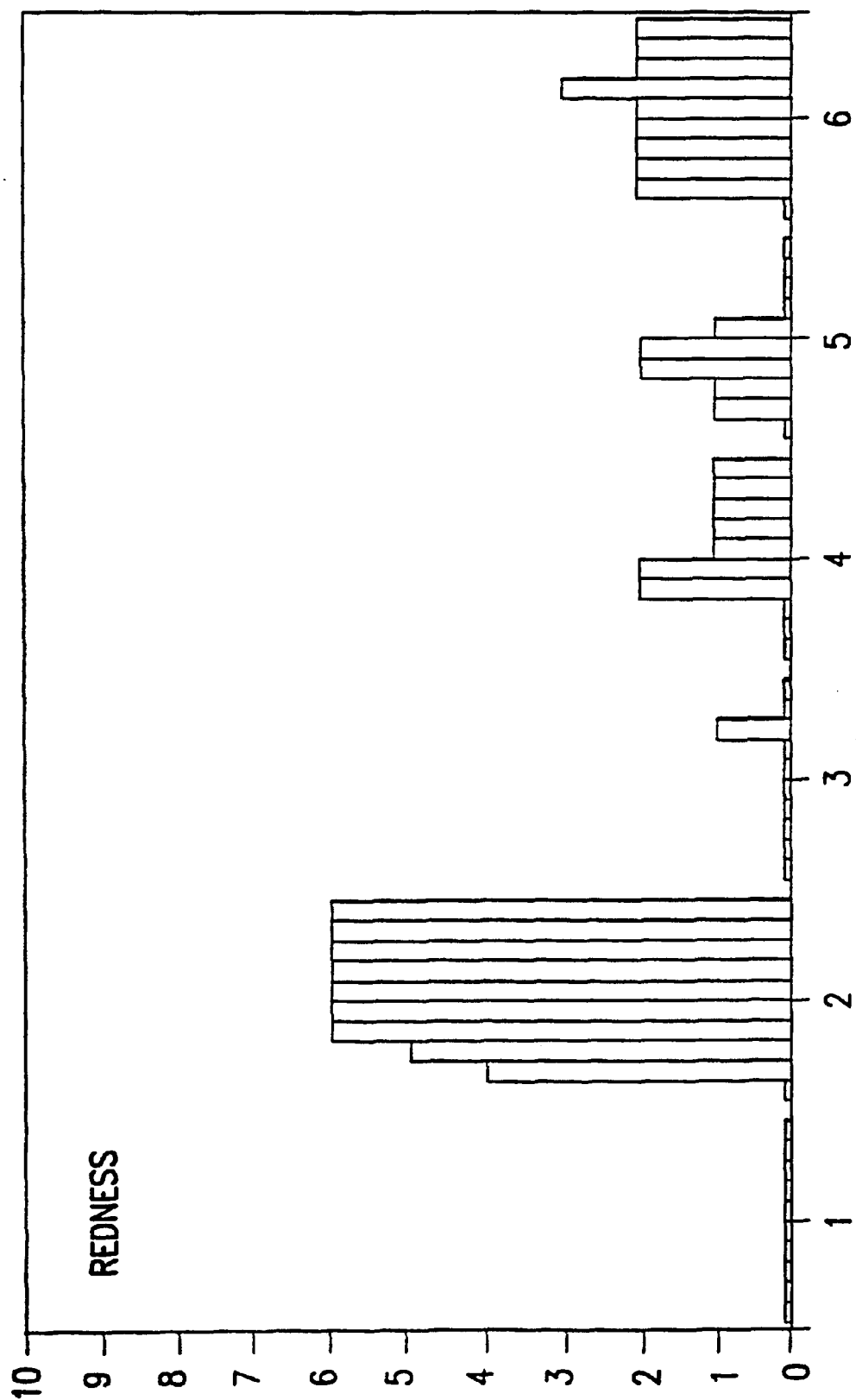

FIG. 2b demonstrates comparative growth of papillomas in 10 sites that received normal CRPV compared to 10 sites that received CRPV treated with N-9. The GMD of each papilloma was measured 3, 4, 5 and 6 weeks after virus inoculation. There was not a difference in the growth of the lesions arising after inoculation with these two virus preparations. In addition, growth rates of control and experimental papillomas in the N-9 animals did not differ from growth rates of control lesions in the SDS treated animals (data not shown).

Effect of SDS Inactivation on the Ability of HPV 11 to Induce Experimental Condylomata in Human Foreskin Epithelial Xenografts. Standard stocks of HPV 11 were used as undiluted virus. These virus stocks normally induce Condylomata in 90–100% of infected xenografts when diluted 1000 fold. In this experiment, 39 µl of undiluted HPV 11 stock was mixed with 1 µl of SDS to a final concentration of 0.05% SDS and then incubated at 37° C. for 10 min. Infection was then carried out for 1 hr and the grafts subsequently transplanted in vivo. Eight animals (16 kidneys) received grafts infected with SDS treated virus and 9 animals (17 kidneys) received normal virus. Table 5 shows the results of the harvested grafts. In the normal infections, 17 of 17 grafts survived and of these, 14 were transformed morphologically upon histologic examination and had typical papillomatous appearance. In animals receiving SDS treated virus, 13 out of 16 xenografts showed viable tissue at the time of harvest and histologic examination of the grafts revealed normal, viable differentiating human epithelium. The latter results are compatible with our previous observations using uninfected grafts in that normal grafts are occasionally resorbed in the mice and do not survive 3 months. We concluded that the SDS had effectively prevented virus infection by inactivation of the virus.

TABLE 5

| *% SDS during treatment | % final SDS | total papillomas | surviving grafts/ transplanted grafts |
|---|---|---|---|
| 0 | 0 | 14 | 17/17 |
| 0.025 | 0.025 | 0 | 13/16 |

*Sterile SDS stocks of 40× the treatment concentration were added to virus aliquots to achieve the treatment concentration.

Effect of SDS Exposure on the Viability of Human Foreskin Xenografts. Because of concern about the potential for SDS to kill human epithelium, control experiments were performed in which split thickness grafts of neonatal foreskin were exposed to 0.05% SDS alone and then subsequently grafted. All conditions in this experiment were identical to those used in the HPV 11 infections with treated virus, except that virus was not present. SDS-exposed grafts (2 animals at each time) were harvested, fixed and sectioned immediately after exposure, and on days 1, 5, 11 and 20 after treatment. Examination of the tissues demonstrated fully viable epithelium on all days and no apparent necrosis associated with detergent exposure. The original split thickness grafts were approximately 1 mm×1 mm×1 mm in size; in addition they were punctured many times with the tip of a needle in order to allow entrance of the HPV 11 and/or the SDS into the epithelial layers. Although it is possible that some epithelial cells may have been damaged or killed during SDS exposure, damage was minimal and epithelial growth in the grafts was normal.

EXAMPLE 2

Cell-Free and Cell-Associated HIV-1 Inactivation

Figure 5A:
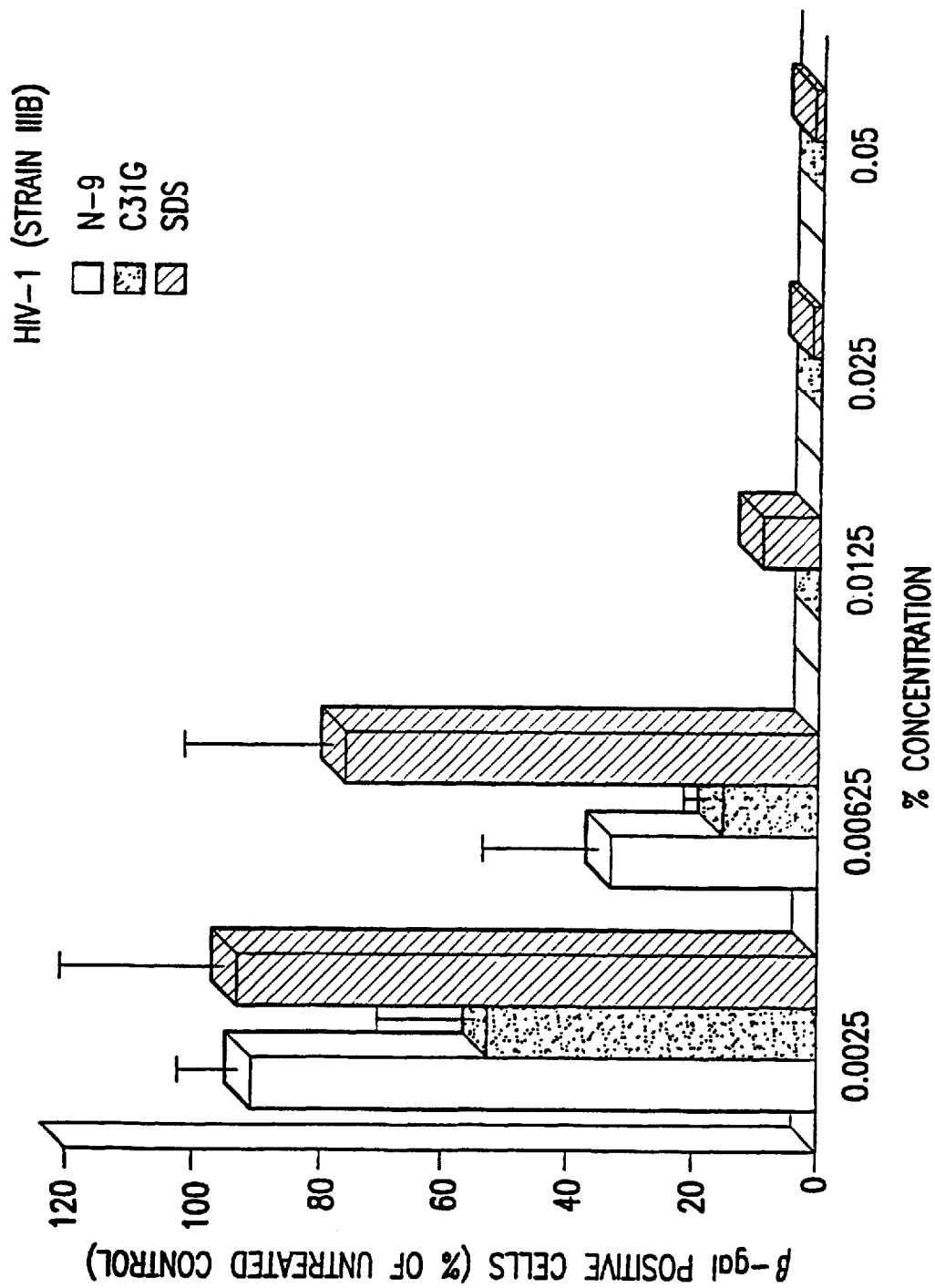
FIG. 5 shows the inactivation of lymphocyte (FIG. 5(a))-, macrophage (FIG. 5(b))-, and dual-tropic (FIG. 5(c)) strains of HIV-1 in the presence of N-9, C31G, and SDS.
Figure 5B:
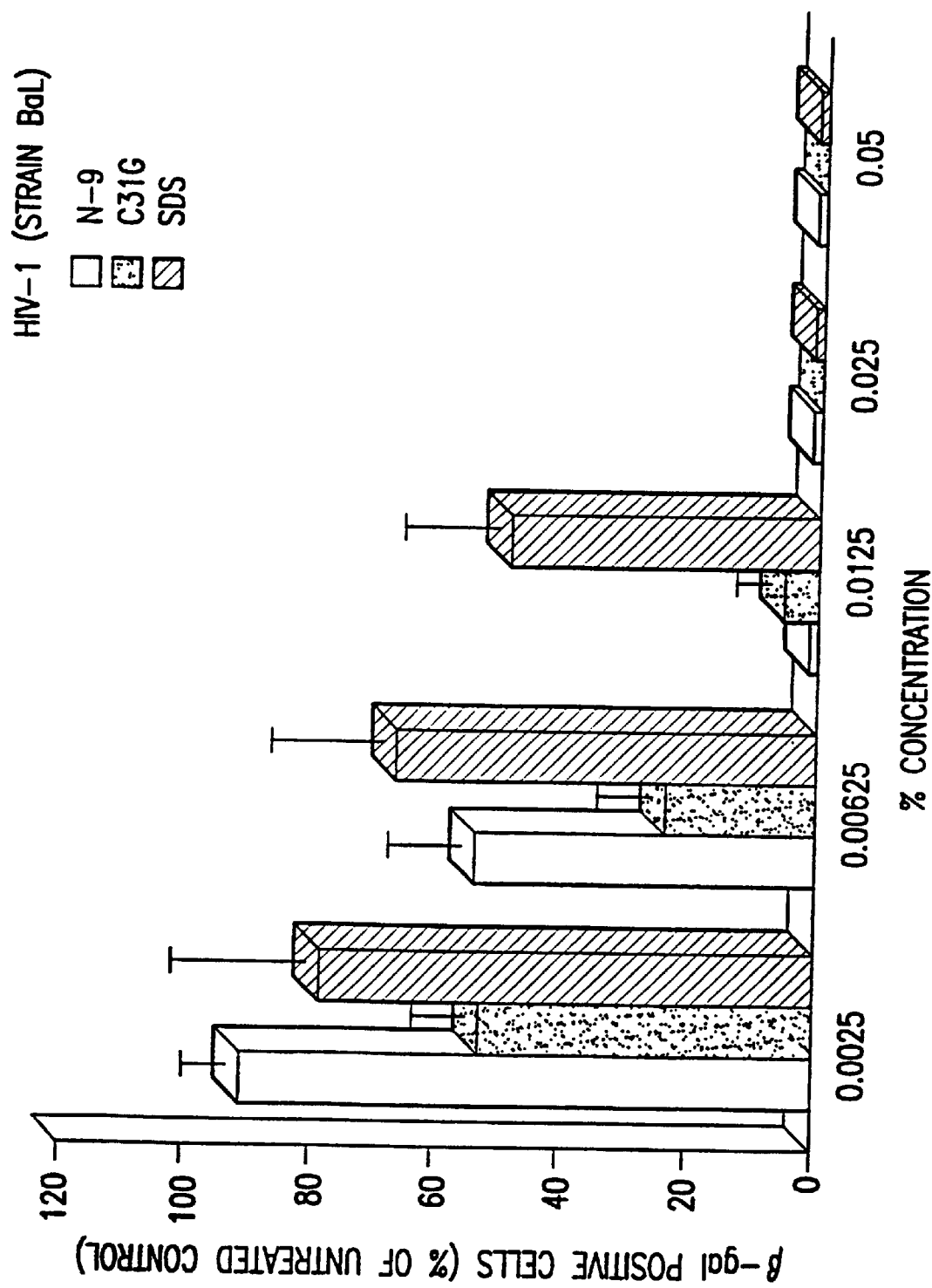
Figure 5C:
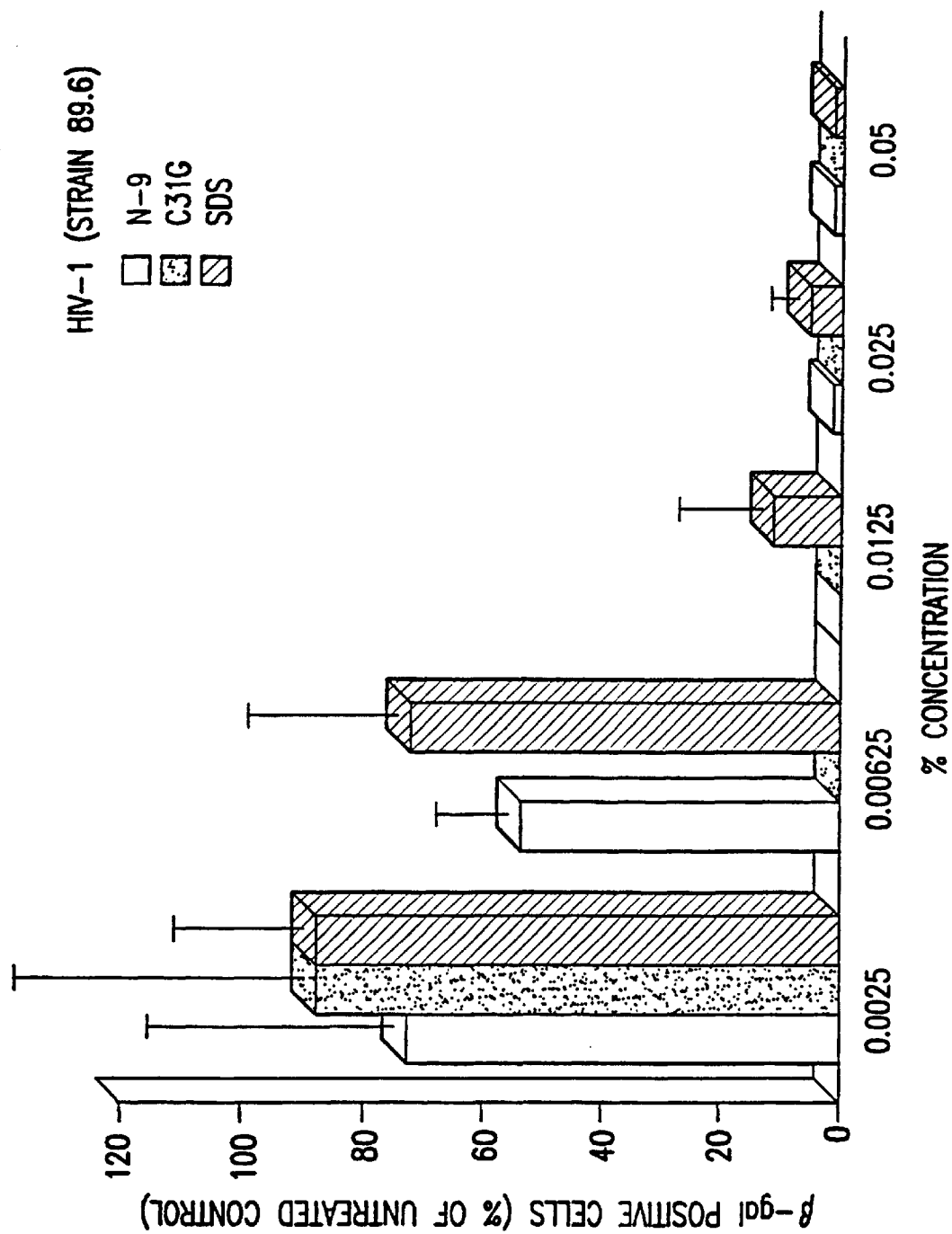

As shown in FIG. 5, lymphocyte-, macrophage- and dual-tropic strains of HIV-1 are inactivated in the presence of N-9, C31G, or SDS. Cell-free HIV-1 strain IIIB (A) was treated with N-9, C31G, or SDS, and used to infect HCLB cells. Cell-free HIV-1 strains BaL (M tropic) (B) and 89.6 (dual tropic) (C) were treated with N-9, C31G or SDS, and used to infect P4-R5 cells. Assays were conducted. Infectivity following exposure is expressed as a percentage relative to the number of β-gal-positive cells in duplicate wells infected with virus incubated in the absence of a microbicidal compound. Results shown in FIG. 5 are the average cell counts for a total of four wells per concentration in two independent experiments.

Figure 6A:
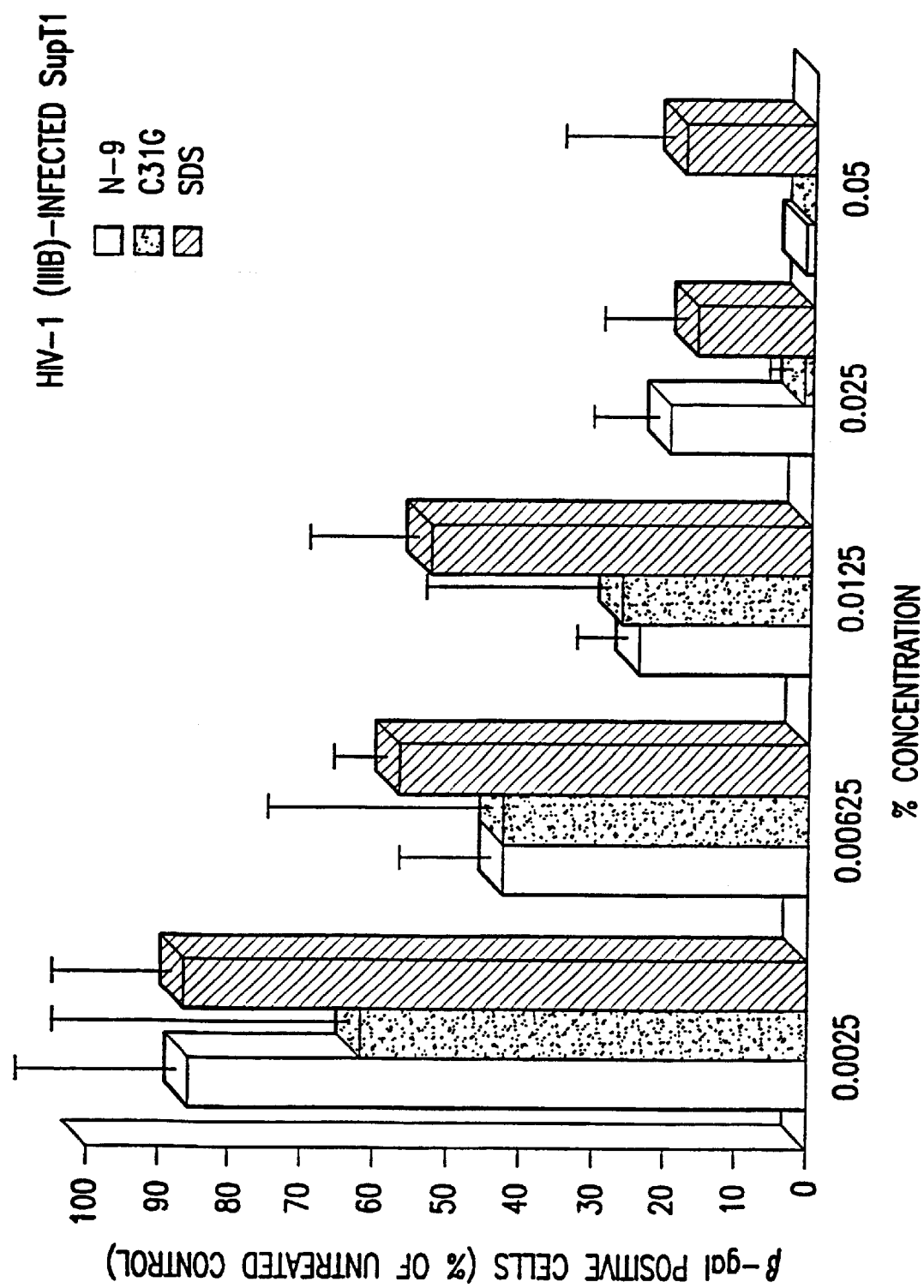
FIG. 6 shows reduction of the cell-associated infectivity (FIG. 6(a)) and viability (FIG. 6(b)) of HIV-1 in infected SupT1 cells via N-9, C31G, and SDS.
Figure 6B:
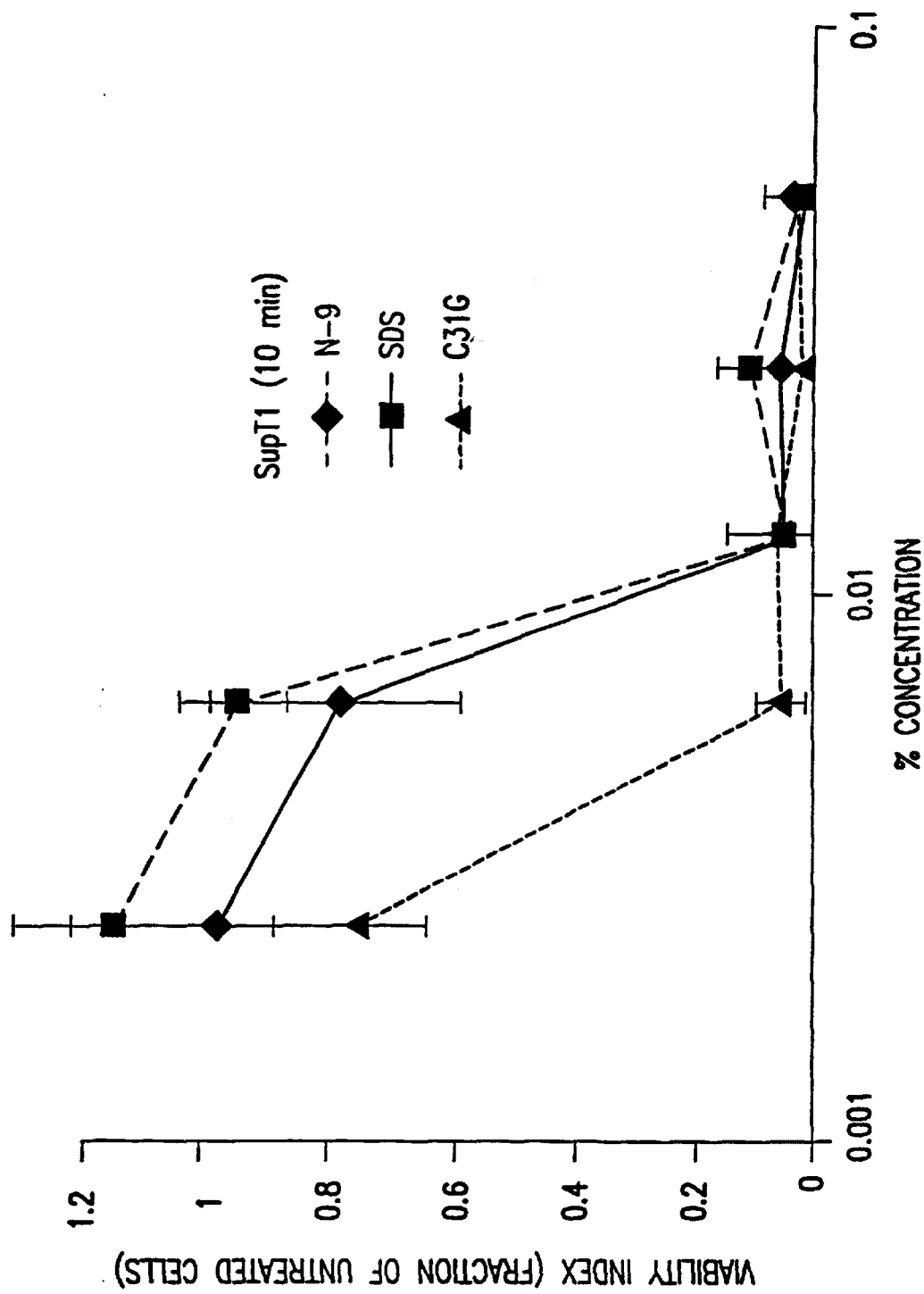

As shown in FIG. 6, N-9, C31G, and SDS can reduce the cell-associated infectivity of HIV-1-infected SupT1 cells. (A) SupT1 T lymphocytes ($8\times10^4$) infected 5 days prior with HIV-1 strain IIIB were pelleted and resuspended in new media to remove cell-free virus. After exposure to selected concentrations of each microbicide for 10 min at 37° C., the cells were diluted 1:10 and co-cultured with HCLB cells for 2 h. Following one wash with PBS to remove the infected lymphocytes, the indicator cells were cultured and assayed. Infectivity following exposure is expressed as a percentage relative to the number of β-gal-positive cells in duplicate wells infected with HIV-1 infected SupT1 cells incubated in the absence of a microbicidal compound. Results shown in FIG. 6(a) are the average cell counts for a total of four wells per concentration in two independent experiments. (B) SupT1 T lymphocytes ($8\times10^4$) were incubated with selected concentrations of each microbicide for 10 min at 37° C., and then diluted 1:10 with new media. Following a 2 h incubation period, the cells were assessed for viability. Cell survival after treatment is expressed as the fraction of viable cells relative to the number of mock-exposed cells. Results shown in FIG. 6(b) are the average of two experiments in which triplicate wells for each concentration were assayed.

EXAMPLE 3

Microbicidal Activity of Alkyl Sulfate Derivatives

The following data show that other members of the alkyl sulfate group, namely lithium dodecyl sulfate, lauric acid and the sodium salt of lauric acid, have anti-papillomavirus activity in the C127 focus assay using bovine papillomavirus. In dose response curves, SDS remains the most potent.

TABLE 6

COMPARISON OF SODIUM DODECYL SULFATE AND LITHIUM DODECYL SULFATE IN THE BPV-1 FOCUS ASSAY

| Treatment | # of FOCI |
|---|---|
| Negative Control | 0, 0, 0, 0 |
| Positive Control | 30, 29, 32, 26 |
| 0.1% SDS Alone | 0, 0, 0, 0 |
| 0.1% LDS Alone | 0, 0, 0, 0 |
| 0.1% SDS + Virus | 0, 0, 0, 0 |
| 0.1% LDS + Virus | 7, 11, 9, 10 |

In all cases, treatment was for 10 min at 37° C., followed by a 1:1000 dilution of the virus preparation.

TABLE 7

COMPARISON OF SODIUM DODECYL SULFATE WITH LAURIC ACID, THE SODIUM SALT OF LAURIC ACID, IN THE BPV-1 FOCUS ASSAY

| Treatment | # of FOCI |
|---|---|
| Negative Control | 0, 0, 0 |
| Positive Control | 50+, 50+, 36 |
| 0.1% SDS + Virus | 0, 0, 0 |
| 0.1% Lauric Acid + Virus | 9, 28 |
| 0.1% NA+ Lauric Acid + Virus | 0, 0, 0 |

In all cases, treatment was for 10 min at 37° C., followed by a 1:1000 dilution of the virus preparation.

EXAMPLE 4

SDS Toxicity and Anti-HSV-2 Activity

The following data represent an in vivo experiment to test both the toxicity and the efficacy of SDS in the protection of mice from vaginal infection with live herpes simplex virus (HSV-2).

GROUP 1 Normal Control
GROUP 2 Live HSV-2 (Approximately $5\times10^6$ Infectious Units)

GROUP 3 Live HSV-2 Plus 4% SDS
GROUP 4 Live HSV-2 Plus 2% SDS
GROUP 5 Live HSV-2 Plus 1% SDS
GROUP 6 Live HSV-2 Plus 0.5% SDS The experiment used outbred, female, Swiss-Webster mice. Mice were anesthetized and then SDS or control solutions (25 µl) was instilled into the vagina using a yellow pipette tip. The SDS was not formulated into a vaginal cream or foam but merely dissolved into phosphate buffered saline. These solutions have low viscosity. Fluids were instilled into groups of 10 mice at one time. Following administration of SDS or control solutions to the group of 10, then an additional 25 µl of virus or control fluid was instilled. Mice were allowed to recover from the anesthesia and then the mice were checked daily for symptoms, beginning on day three and until 12 days after inoculation. Vaginal swabs were also performed on the mice on a daily basis, beginning on day three, in order to determine shedding of virus. FIGS. 3A–3G show the total symptoms per group on days 3 through 12 for each of the following symptoms: swelling, vaginal exudate, redness, death, leg paralysis, perianal hair loss and any symptom.

The results clearly show that all concentrations of SDS provided significant protection from HSV-2 inoculation of the vagina. In addition a dose response was evident for every symptom checked; with 4% SDS providing the most protection. The results of determinations of virus shedding are not shown but confirm and support these data.

EXAMPLE 5

Spermicidal Activity

The following data represent an in vitro experiment to test the efficacy of SDS and other detergents as spermicidal agents. Frozen samples of bull semen were obtained, thawed and placed in a test tube. Aliquots were taken out and put in a separate test tube where they were mixed with detergent (SDS, C31G, N-9 or a mixture of SDS and N-9) to a final percent as listed in Tables 8 and 9 below. After mixing, the samples were immediately placed on a microscope slide and visually examined for sperm movement. The experiment was conducted one sample at a time so that the visual examination was conducted immediately after addition of detergent to the sample. As a result, indications in the table of complete inactivation indicate virtually instantaneous inactivation of the sperm. Delayed inactivation indicates delay of approximately 10 minutes for those sperm cells that did not immediately stop swimming. Occasional swimmers means very few, on the order of approximately 1% of the population of sperm present in the sample, indicating approximately 99% of the sperm were inactivated by the detergent.

TABLE 8

Bovine Sperm Motility Following Detergent Addition

|      | N-9* | C31G** | SDS*** | N-9/SDS |
|------|------|--------|--------|---------|
| 2%   | —    | —      | —      |         |
| 1%   | —    | —      | —      |         |
| 0.5% | —    | —      | —      |         |
| 0.025% | —  | —      | —      |         |
| 0.0125% | +++ | +/−  | +/− (delayed) | +/− (delayed) |

*No Coagulation
**Major Coagulation
***Moderate Coagulation

When coaguation was present, amount decreased with decreasing concentration.

| Key | |
|-----|---|
| +++ | Vigorous swimming |
| ++/− | Many swimmers/some dead |
| +/− | Occasional swimmer/most dead |
| − | All dead |

TABLE 9

Bovine Sperm Motility Following Detergent Addition

|        | N-9  | C31G | SDS  | SDS/N-9 | SDS/C31G | N-9/C31G |
|--------|------|------|------|---------|----------|----------|
| 2%     | −    | −    | +/−  | +/−     | +/−      | +/−      |
| 1%     | ++/− | +/−  | ++/− | ++/−    | ++/−     | ++/−     |
| 0.5%   | +++  | +++  | ++/− | +++     | +++      |          |
| 0.25%  | +++  | +++  | ++/− | +++     | +++      |          |
| 0.125% | +++  | +++  | ++/− | +++     | +++      |          |

Key
+++Vigorous swimming
++/−Many swimmers/some dead
+/−Occasional swimmer/most dead
−All dead

We claim:

1. An article of manufacture comprising a substrate and a compound for reducing the titer of viruses in contact with said compound, wherein said compound is selected from the group consisting of sodium dodecyl sulfate, lithium dodecyl sulfate, lauric acid and salts thereof and is present in an amount sufficient to reduce said viral titer by at least 99.9%.

2. The article of manufacture of claim 1 wherein said compound is impregnated in said substrate.

3. The article of manufacture of claim 1 wherein said compound is in a coating on said substrate.

4. The article of manufacture of claim 1 wherein said compound is covalently bound to said substrate.

5. The article of manufacture of claim 1 wherein said article is a container for a biological fluid.

6. The article of manufacture of claim 1, wherein said article is a condom.

* * * * *